United States Patent
Rathor et al.

(10) Patent No.: US 10,027,689 B1
(45) Date of Patent: Jul. 17, 2018

(54) INTERACTIVE INFECTION VISUALIZATION FOR IMPROVED EXPLOIT DETECTION AND SIGNATURE GENERATION FOR MALWARE AND MALWARE FAMILIES

(71) Applicant: FireEye, Inc., Milpitas, CA (US)

(72) Inventors: Hirendra Rathor, Bangalore (IN); Kaushal Dalal, Bangalore (IN); Anil Gupta, Bangalore (IN)

(73) Assignee: FireEye, Inc., Milpitas, CA (US)

( * ) Notice: Subject to any disclaimer, the term of this patent is extended or adjusted under 35 U.S.C. 154(b) by 50 days.

(21) Appl. No.: 14/500,587

(22) Filed: Sep. 29, 2014

(51) Int. Cl.
*H04L 29/06* (2006.01)
*G06F 3/0481* (2013.01)
(Continued)

(52) U.S. Cl.
CPC ........ *H04L 63/1416* (2013.01); *G06F 3/0481* (2013.01); *G06F 21/566* (2013.01); *G06F 19/18* (2013.01); *G06F 2201/86* (2013.01)

(58) Field of Classification Search
CPC . H04L 63/1416; G06F 3/0481; G06F 21/552; G06F 21/554; G06F 21/566; G06F 2201/86; G06F 19/18
See application file for complete search history.

(56) References Cited

U.S. PATENT DOCUMENTS 4,292,580 A 9/1981 Ott et al.
5,175,732 A 12/1992 Hendel et al.
(Continued)

FOREIGN PATENT DOCUMENTS

GB 2439806 A 1/2008
GB 2490431 A 10/2012
(Continued)

OTHER PUBLICATIONS

Adobe Systems Incorporated, "PDF 32000-1:2008, Document management—Portable document format—Part1:PDF 1.7", First Edition, Jul. 1, 2008, 756 pages.

(Continued)

*Primary Examiner* — Eleni A Shiferaw
*Assistant Examiner* — Sher A Khan
(74) *Attorney, Agent, or Firm* — Rutan & Tucker, LLP

(57) ABSTRACT

According to one embodiment, a malware detection and visualization system comprises one or more processors; and a storage module communicatively coupled to the one or more processors, the storage module comprises logic, upon execution by the one or more processors, that accesses a first set of information that comprises (i) information directed to a plurality of observed events and (ii) information directed to one or more relationships that identify an association between different observed events of the plurality of observed events; and generates a reference model based on the first set of information, the reference model comprises at least a first event of the plurality of observed events, a second event of the plurality of observed events, and a first relationship that identifies that the second event is based on the first event, wherein at least one of (i) the plurality of observed events or (ii) the one or more relationships constitutes an anomalous behavior is provided.

52 Claims, 19 Drawing Sheets

(51) Int. Cl.
*G06F 21/56* (2013.01)
*G06F 19/18* (2011.01)

(56) References Cited

U.S. PATENT DOCUMENTS

| | | |
|---|---|---|
| 5,440,723 A | 8/1995 | Arnold et al. |
| 5,490,249 A | 2/1996 | Miller |
| 5,657,473 A | 8/1997 | Killeen et al. |
| 5,842,002 A | 11/1998 | Schnurer et al. |
| 5,978,917 A | 11/1999 | Chi |
| 6,088,803 A | 7/2000 | Tso et al. |
| 6,094,677 A | 7/2000 | Capek et al. |
| 6,108,799 A | 8/2000 | Boulay et al. |
| 6,118,382 A | 9/2000 | Hibbs et al. |
| 6,269,330 B1 | 7/2001 | Cidon et al. |
| 6,272,641 B1 | 8/2001 | Ji |
| 6,279,113 B1 | 8/2001 | Vaidya |
| 6,298,445 B1 | 10/2001 | Shostack et al. |
| 6,357,008 B1 | 3/2002 | Nachenberg |
| 6,417,774 B1 | 7/2002 | Hibbs et al. |
| 6,424,627 B1 | 7/2002 | S.o slashed.rhaug et al. |
| 6,442,696 B1 | 8/2002 | Wray et al. |
| 6,484,315 B1 | 11/2002 | Ziese |
| 6,487,666 B1 | 11/2002 | Shanklin et al. |
| 6,493,756 B1 | 12/2002 | O'Brien et al. |
| 6,550,012 B1 | 4/2003 | Villa et al. |
| 6,700,497 B2 | 3/2004 | Hibbs et al. |
| 6,775,657 B1 | 8/2004 | Baker |
| 6,831,893 B1 | 12/2004 | Ben Nun et al. |
| 6,832,367 B1 | 12/2004 | Choi et al. |
| 6,895,550 B2 | 5/2005 | Kanchirayappa et al. |
| 6,898,632 B2 | 5/2005 | Gordy et al. |
| 6,907,396 B1 | 6/2005 | Muttik et al. |
| 6,941,348 B2 | 9/2005 | Petry et al. |
| 6,971,097 B1 | 11/2005 | Wallman |
| 6,981,279 B1 | 12/2005 | Arnold et al. |
| 6,995,665 B2 | 2/2006 | Appelt et al. |
| 7,007,107 B1 | 2/2006 | Ivchenko et al. |
| 7,028,179 B2 | 4/2006 | Anderson et al. |
| 7,043,757 B2 | 5/2006 | Hoefelmeyer et al. |
| 7,069,316 B1 | 6/2006 | Gryaznov |
| 7,080,407 B1 | 7/2006 | Zhao et al. |
| 7,080,408 B1 | 7/2006 | Pak et al. |
| 7,093,239 B1 | 8/2006 | van der Made |
| 7,096,498 B2 | 8/2006 | Judge |
| 7,100,201 B2 | 8/2006 | Izatt |
| 7,107,617 B2 | 9/2006 | Hursey et al. |
| 7,159,149 B2 | 1/2007 | Spiegel et al. |
| 7,213,260 B2 | 5/2007 | Judge |
| 7,231,596 B2 * | 6/2007 | Koren ............... G06F 17/30893 707/E17.12 |
| 7,231,667 B2 | 6/2007 | Jordan |
| 7,240,364 B1 | 7/2007 | Branscomb et al. |
| 7,240,368 B1 | 7/2007 | Roesch et al. |
| 7,243,371 B1 | 7/2007 | Kasper et al. |
| 7,249,175 B1 | 7/2007 | Donaldson |
| 7,287,278 B2 | 10/2007 | Liang |
| 7,308,716 B2 | 12/2007 | Danford et al. |
| 7,328,453 B2 | 2/2008 | Merkle, Jr. et al. |
| 7,346,486 B2 | 3/2008 | Ivancic et al. |
| 7,356,736 B2 | 4/2008 | Natvig |
| 7,386,888 B2 | 6/2008 | Liang et al. |
| 7,392,542 B2 | 6/2008 | Bucher |
| 7,418,729 B2 | 8/2008 | Szor |
| 7,428,300 B1 | 9/2008 | Drew et al. |
| 7,441,272 B2 | 10/2008 | Durham et al. |
| 7,448,084 B1 | 11/2008 | Apap et al. |
| 7,458,098 B2 | 11/2008 | Judge et al. |
| 7,464,404 B2 | 12/2008 | Carpenter et al. |
| 7,464,407 B2 | 12/2008 | Nakae et al. |
| 7,467,408 B1 | 12/2008 | O'Toole, Jr. |
| 7,478,428 B1 | 1/2009 | Thomlinson |
| 7,480,773 B1 | 1/2009 | Reed |
| 7,487,543 B2 | 2/2009 | Arnold et al. |
| 7,496,960 B1 | 2/2009 | Chen et al. |
| 7,496,961 B2 | 2/2009 | Zimmer et al. |
| 7,519,990 B1 | 4/2009 | Xie |
| 7,523,493 B2 | 4/2009 | Liang et al. |
| 7,530,104 B1 | 5/2009 | Thrower et al. |
| 7,540,025 B2 | 5/2009 | Tzadikario |
| 7,565,550 B2 | 7/2009 | Liang et al. |
| 7,568,233 B1 | 7/2009 | Szor et al. |
| 7,584,455 B2 | 9/2009 | Ball |
| 7,603,715 B2 | 10/2009 | Costa et al. |
| 7,607,171 B1 | 10/2009 | Marsden et al. |
| 7,639,714 B2 | 12/2009 | Stolfo et al. |
| 7,644,441 B2 | 1/2010 | Schmid et al. |
| 7,657,419 B2 | 2/2010 | van der Made |
| 7,676,841 B2 | 3/2010 | Sobchuk et al. |
| 7,680,703 B1 * | 3/2010 | Smith .................. G06Q 10/06 705/26.8 |
| 7,698,548 B2 | 4/2010 | Shelest et al. |
| 7,707,633 B2 | 4/2010 | Danford et al. |
| 7,712,136 B2 | 5/2010 | Sprosts et al. |
| 7,730,011 B1 | 6/2010 | Deninger et al. |
| 7,739,740 B1 | 6/2010 | Nachenberg et al. |
| 7,779,463 B2 | 8/2010 | Stolfo et al. |
| 7,784,097 B1 | 8/2010 | Stolfo et al. |
| 7,836,502 B1 | 11/2010 | Zhao et al. |
| 7,849,506 B1 | 12/2010 | Dansey et al. |
| 7,854,007 B2 | 12/2010 | Sprosts et al. |
| 7,869,073 B2 | 1/2011 | Oshima |
| 7,877,803 B2 | 1/2011 | Enstone et al. |
| 7,904,959 B2 | 3/2011 | Sidiroglou et al. |
| 7,908,660 B2 | 3/2011 | Bahl |
| 7,930,738 B1 | 4/2011 | Petersen |
| 7,937,761 B1 | 5/2011 | Bennett |
| 7,949,849 B2 | 5/2011 | Lowe et al. |
| 7,996,556 B2 | 8/2011 | Raghavan et al. |
| 7,996,836 B1 | 8/2011 | McCorkendale et al. |
| 7,996,904 B1 | 8/2011 | Chiueh et al. |
| 7,996,905 B2 | 8/2011 | Arnold et al. |
| 8,006,305 B2 | 8/2011 | Aziz |
| 8,010,667 B2 | 8/2011 | Zhang et al. |
| 8,020,206 B2 | 9/2011 | Hubbard et al. |
| 8,028,338 B1 | 9/2011 | Schneider et al. |
| 8,042,184 B1 | 10/2011 | Batenin |
| 8,045,094 B2 | 10/2011 | Teragawa |
| 8,045,458 B2 | 10/2011 | Alperovitch et al. |
| 8,069,484 B2 | 11/2011 | McMillan et al. |
| 8,087,086 B1 | 12/2011 | Lai et al. |
| 8,171,553 B2 | 5/2012 | Aziz et al. |
| 8,176,049 B2 | 5/2012 | Deninger et al. |
| 8,176,480 B1 | 5/2012 | Spertus |
| 8,204,984 B1 | 6/2012 | Aziz et al. |
| 8,214,905 B1 | 7/2012 | Doukhvalov et al. |
| 8,220,055 B1 | 7/2012 | Kennedy |
| 8,225,373 B2 | 7/2012 | Kraemer |
| 8,233,882 B2 | 7/2012 | Rogel |
| 8,234,640 B1 | 7/2012 | Fitzgerald et al. |
| 8,234,709 B2 | 7/2012 | Viljoen et al. |
| 8,239,944 B1 | 8/2012 | Nachenberg et al. |
| 8,260,914 B1 | 9/2012 | Ranjan |
| 8,266,091 B1 | 9/2012 | Gubin et al. |
| 8,286,251 B2 | 10/2012 | Eker et al. |
| 8,291,499 B2 | 10/2012 | Aziz et al. |
| 8,307,435 B1 | 11/2012 | Mann et al. |
| 8,307,443 B2 | 11/2012 | Wang et al. |
| 8,312,545 B2 | 11/2012 | Tuvell et al. |
| 8,321,936 B1 | 11/2012 | Green et al. |
| 8,321,941 B2 | 11/2012 | Tuvell et al. |
| 8,332,571 B1 | 12/2012 | Edwards, Sr. |
| 8,365,286 B2 | 1/2013 | Poston |
| 8,365,297 B1 | 1/2013 | Parshin et al. |
| 8,370,938 B1 | 2/2013 | Daswani et al. |
| 8,370,939 B2 | 2/2013 | Zaitsev et al. |
| 8,375,444 B2 | 2/2013 | Aziz et al. |
| 8,381,299 B2 | 2/2013 | Stolfo et al. |
| 8,402,529 B1 | 3/2013 | Green et al. |
| 8,464,340 B2 | 6/2013 | Ahn et al. |
| 8,479,174 B2 | 7/2013 | Chiriac |
| 8,479,276 B1 | 7/2013 | Vaystikh et al. |
| 8,479,291 B1 | 7/2013 | Bodke |
| 8,510,827 B1 | 8/2013 | Leake et al. |

(56) References Cited

U.S. PATENT DOCUMENTS

| | | |
|---|---|---|
| 8,510,828 B1 | 8/2013 | Guo et al. |
| 8,510,842 B2 | 8/2013 | Amit et al. |
| 8,516,478 B1 | 8/2013 | Edwards et al. |
| 8,516,590 B1 | 8/2013 | Ranadive et al. |
| 8,516,593 B2 | 8/2013 | Aziz |
| 8,516,594 B2 * | 8/2013 | Bennett ................. G06F 21/577 713/188 |
| 8,520,015 B2 * | 8/2013 | Krishna ................... G06F 9/541 345/522 |
| 8,522,348 B2 | 8/2013 | Chen et al. |
| 8,528,086 B1 | 9/2013 | Aziz |
| 8,533,824 B2 | 9/2013 | Hutton et al. |
| 8,539,582 B1 | 9/2013 | Aziz et al. |
| 8,549,638 B2 | 10/2013 | Aziz |
| 8,555,391 B1 | 10/2013 | Demir et al. |
| 8,561,177 B1 | 10/2013 | Aziz et al. |
| 8,566,946 B1 | 10/2013 | Aziz et al. |
| 8,584,094 B2 | 11/2013 | Dadhia et al. |
| 8,584,234 B1 | 11/2013 | Sobel et al. |
| 8,584,239 B2 | 11/2013 | Aziz et al. |
| 8,595,834 B2 | 11/2013 | Xie et al. |
| 8,627,476 B1 | 1/2014 | Satish et al. |
| 8,635,696 B1 | 1/2014 | Aziz |
| 8,682,054 B2 | 3/2014 | Xue et al. |
| 8,682,812 B1 | 3/2014 | Ranjan |
| 8,689,333 B2 | 4/2014 | Aziz |
| 8,695,096 B1 | 4/2014 | Zhang |
| 8,713,631 B1 | 4/2014 | Pavlyushchik |
| 8,713,681 B2 | 4/2014 | Silberman et al. |
| 8,726,392 B1 | 5/2014 | McCorkendale et al. |
| 8,739,280 B2 | 5/2014 | Chess et al. |
| 8,776,229 B1 | 7/2014 | Aziz |
| 8,782,792 B1 | 7/2014 | Bodke |
| 8,787,532 B1 | 7/2014 | Adam |
| 8,789,172 B2 | 7/2014 | Stolfo et al. |
| 8,789,178 B2 | 7/2014 | Kejriwal et al. |
| 8,793,787 B2 | 7/2014 | Ismael et al. |
| 8,805,947 B1 | 8/2014 | Kuzkin et al. |
| 8,806,647 B1 | 8/2014 | Daswani et al. |
| 8,832,829 B2 | 9/2014 | Manni et al. |
| 8,850,570 B1 | 9/2014 | Ramzan |
| 8,850,571 B2 | 9/2014 | Staniford et al. |
| 8,881,234 B2 | 11/2014 | Narasimhan et al. |
| 8,881,282 B1 | 11/2014 | Aziz et al. |
| 8,898,788 B1 | 11/2014 | Aziz et al. |
| 8,935,779 B2 | 1/2015 | Manni et al. |
| 8,984,638 B1 | 3/2015 | Aziz et al. |
| 8,990,939 B2 | 3/2015 | Staniford et al. |
| 8,990,944 B1 | 3/2015 | Singh et al. |
| 8,997,219 B2 | 3/2015 | Staniford et al. |
| 9,009,822 B1 | 4/2015 | Ismael et al. |
| 9,009,823 B1 | 4/2015 | Ismael et al. |
| 9,027,135 B1 | 5/2015 | Aziz |
| 9,071,638 B1 | 6/2015 | Aziz et al. |
| 9,104,867 B1 | 8/2015 | Thioux et al. |
| 9,106,694 B2 | 8/2015 | Aziz et al. |
| 9,112,895 B1 * | 8/2015 | Lin .................... H04L 63/1416 |
| 9,118,714 B1 * | 8/2015 | Thomson ............ H04L 63/1441 |
| 9,118,715 B2 | 8/2015 | Staniford et al. |
| 9,195,965 B2 * | 11/2015 | Sitrick ................. G06Q 10/101 |
| 9,223,972 B1 | 12/2015 | Vincent et al. |
| 9,239,922 B1 * | 1/2016 | Zhu ........................ G06F 21/56 |
| 9,251,343 B1 | 2/2016 | Vincent et al. |
| 9,270,689 B1 * | 2/2016 | Wang .................... H04L 63/145 |
| 9,300,686 B2 | 3/2016 | Pidathala et al. |
| 9,306,960 B1 | 4/2016 | Aziz |
| 9,306,974 B1 | 4/2016 | Aziz et al. |
| 2001/0005889 A1 | 6/2001 | Albrecht |
| 2001/0047326 A1 | 11/2001 | Broadbent et al. |
| 2002/0018903 A1 | 2/2002 | Kokubo et al. |
| 2002/0038430 A1 | 3/2002 | Edwards et al. |
| 2002/0091819 A1 | 7/2002 | Melchione et al. |
| 2002/0095607 A1 | 7/2002 | Lin-Hendel |
| 2002/0116627 A1 | 8/2002 | Tarbotton et al. |
| 2002/0144156 A1 | 10/2002 | Copeland |
| 2002/0162015 A1 | 10/2002 | Tang |
| 2002/0166063 A1 | 11/2002 | Lachman et al. |
| 2002/0169952 A1 | 11/2002 | DiSanto et al. |
| 2002/0184528 A1 | 12/2002 | Shevenell et al. |
| 2002/0188887 A1 | 12/2002 | Largman et al. |
| 2002/0194490 A1 | 12/2002 | Halperin et al. |
| 2003/0074578 A1 | 4/2003 | Ford et al. |
| 2003/0084318 A1 | 5/2003 | Schertz |
| 2003/0101381 A1 | 5/2003 | Mateev et al. |
| 2003/0115483 A1 | 6/2003 | Liang |
| 2003/0188190 A1 | 10/2003 | Aaron et al. |
| 2003/0191957 A1 | 10/2003 | Hypponen et al. |
| 2003/0200460 A1 | 10/2003 | Morota et al. |
| 2003/0212902 A1 | 11/2003 | van der Made |
| 2003/0229801 A1 | 12/2003 | Kouznetsov et al. |
| 2003/0237000 A1 | 12/2003 | Denton et al. |
| 2004/0003323 A1 | 1/2004 | Bennett et al. |
| 2004/0015712 A1 | 1/2004 | Szor |
| 2004/0019832 A1 | 1/2004 | Arnold et al. |
| 2004/0047356 A1 | 3/2004 | Bauer |
| 2004/0083408 A1 | 4/2004 | Spiegel et al. |
| 2004/0088581 A1 | 5/2004 | Brawn et al. |
| 2004/0093513 A1 | 5/2004 | Cantrell et al. |
| 2004/0111531 A1 | 6/2004 | Staniford et al. |
| 2004/0117478 A1 | 6/2004 | Triulzi et al. |
| 2004/0117624 A1 | 6/2004 | Brandt et al. |
| 2004/0128355 A1 | 7/2004 | Chao et al. |
| 2004/0143749 A1 * | 7/2004 | Tajalli ................... G06F 21/566 726/23 |
| 2004/0165588 A1 | 8/2004 | Pandya |
| 2004/0236963 A1 | 11/2004 | Danford et al. |
| 2004/0243349 A1 | 12/2004 | Greifeneder et al. |
| 2004/0243829 A1 * | 12/2004 | Jordan ................... G06F 21/566 726/24 |
| 2004/0249911 A1 | 12/2004 | Alkhatib et al. |
| 2004/0255161 A1 | 12/2004 | Cavanaugh |
| 2004/0268147 A1 | 12/2004 | Wiederin et al. |
| 2005/0005159 A1 | 1/2005 | Oliphant |
| 2005/0021740 A1 | 1/2005 | Bar et al. |
| 2005/0033960 A1 | 2/2005 | Vialen et al. |
| 2005/0033989 A1 | 2/2005 | Poletto et al. |
| 2005/0050148 A1 | 3/2005 | Mohammadioun et al. |
| 2005/0086523 A1 | 4/2005 | Zimmer et al. |
| 2005/0091513 A1 | 4/2005 | Mitomo et al. |
| 2005/0091533 A1 | 4/2005 | Omote et al. |
| 2005/0091652 A1 | 4/2005 | Ross et al. |
| 2005/0108562 A1 | 5/2005 | Khazan et al. |
| 2005/0114663 A1 | 5/2005 | Cornell et al. |
| 2005/0125195 A1 | 6/2005 | Brendel |
| 2005/0149726 A1 | 7/2005 | Joshi et al. |
| 2005/0157662 A1 | 7/2005 | Bingham et al. |
| 2005/0183143 A1 * | 8/2005 | Anderholm ............ G06F 11/32 726/22 |
| 2005/0201297 A1 | 9/2005 | Peikari |
| 2005/0203881 A1 * | 9/2005 | Sakamoto ............. G06F 21/552 |
| 2005/0210533 A1 | 9/2005 | Copeland et al. |
| 2005/0238005 A1 | 10/2005 | Chen et al. |
| 2005/0240781 A1 | 10/2005 | Gassoway |
| 2005/0262562 A1 | 11/2005 | Gassoway |
| 2005/0265331 A1 | 12/2005 | Stolfo |
| 2005/0283839 A1 | 12/2005 | Cowburn |
| 2006/0010495 A1 | 1/2006 | Cohen et al. |
| 2006/0015416 A1 | 1/2006 | Hoffman et al. |
| 2006/0015715 A1 | 1/2006 | Anderson |
| 2006/0015747 A1 | 1/2006 | Van de Ven |
| 2006/0021029 A1 | 1/2006 | Brickell et al. |
| 2006/0021054 A1 | 1/2006 | Costa et al. |
| 2006/0031476 A1 | 2/2006 | Mathes et al. |
| 2006/0047665 A1 | 3/2006 | Neil |
| 2006/0070130 A1 | 3/2006 | Costea et al. |
| 2006/0075496 A1 | 4/2006 | Carpenter et al. |
| 2006/0095968 A1 | 5/2006 | Portolani et al. |
| 2006/0101516 A1 | 5/2006 | Sudaharan et al. |
| 2006/0101517 A1 | 5/2006 | Banzhof et al. |
| 2006/0117385 A1 | 6/2006 | Mester et al. |
| 2006/0123477 A1 | 6/2006 | Raghavan et al. |
| 2006/0143709 A1 | 6/2006 | Brooks et al. |
| 2006/0150249 A1 | 7/2006 | Gassen et al. |
| 2006/0161983 A1 | 7/2006 | Cothrell et al. |

(56) References Cited

U.S. PATENT DOCUMENTS

| | | |
|---|---|---|
| 2006/0161987 A1 | 7/2006 | Levy-Yurista |
| 2006/0161989 A1 | 7/2006 | Reshef et al. |
| 2006/0164199 A1 | 7/2006 | Gilde et al. |
| 2006/0173992 A1 | 8/2006 | Weber et al. |
| 2006/0179147 A1 | 8/2006 | Tran et al. |
| 2006/0184632 A1 | 8/2006 | Marino et al. |
| 2006/0191010 A1 | 8/2006 | Benjamin |
| 2006/0195227 A1* | 8/2006 | Sabe .................. G05B 13/021 700/245 |
| 2006/0221956 A1 | 10/2006 | Narayan et al. |
| 2006/0236393 A1 | 10/2006 | Kramer et al. |
| 2006/0242709 A1 | 10/2006 | Seinfeld et al. |
| 2006/0248519 A1 | 11/2006 | Jaeger et al. |
| 2006/0248582 A1 | 11/2006 | Panjwani et al. |
| 2006/0251104 A1 | 11/2006 | Koga |
| 2006/0288417 A1 | 12/2006 | Bookbinder et al. |
| 2006/0294589 A1* | 12/2006 | Achanta .............. G06F 21/564 726/24 |
| 2007/0006288 A1 | 1/2007 | Mayfield et al. |
| 2007/0006313 A1 | 1/2007 | Porras et al. |
| 2007/0011174 A1 | 1/2007 | Takaragi et al. |
| 2007/0016951 A1 | 1/2007 | Piccard et al. |
| 2007/0033645 A1 | 2/2007 | Jones |
| 2007/0038943 A1 | 2/2007 | FitzGerald et al. |
| 2007/0064689 A1 | 3/2007 | Shin et al. |
| 2007/0074169 A1 | 3/2007 | Chess et al. |
| 2007/0094730 A1 | 4/2007 | Bhikkaji et al. |
| 2007/0101435 A1 | 5/2007 | Konanka et al. |
| 2007/0128855 A1 | 6/2007 | Cho et al. |
| 2007/0142030 A1 | 6/2007 | Sinha et al. |
| 2007/0143827 A1 | 6/2007 | Nicodemus et al. |
| 2007/0156895 A1 | 7/2007 | Vuong |
| 2007/0157180 A1 | 7/2007 | Tillmann et al. |
| 2007/0157306 A1 | 7/2007 | Elrod et al. |
| 2007/0168988 A1 | 7/2007 | Eisner et al. |
| 2007/0171824 A1 | 7/2007 | Ruello et al. |
| 2007/0174911 A1* | 7/2007 | Kronenberg ........... G06F 21/56 726/22 |
| 2007/0174915 A1 | 7/2007 | Gribble et al. |
| 2007/0192500 A1 | 8/2007 | Lum |
| 2007/0192858 A1 | 8/2007 | Lum |
| 2007/0198275 A1 | 8/2007 | Malden et al. |
| 2007/0208822 A1 | 9/2007 | Wang et al. |
| 2007/0220607 A1 | 9/2007 | Sprosts et al. |
| 2007/0240218 A1 | 10/2007 | Tuvell et al. |
| 2007/0240219 A1 | 10/2007 | Tuvell et al. |
| 2007/0240220 A1 | 10/2007 | Tuvell et al. |
| 2007/0240222 A1 | 10/2007 | Tuvell et al. |
| 2007/0250930 A1 | 10/2007 | Aziz et al. |
| 2007/0256132 A2 | 11/2007 | Oliphant |
| 2007/0271446 A1 | 11/2007 | Nakamura |
| 2008/0005782 A1 | 1/2008 | Aziz |
| 2008/0028463 A1 | 1/2008 | Dagon et al. |
| 2008/0032556 A1 | 2/2008 | Schreier |
| 2008/0040710 A1 | 2/2008 | Chiriac |
| 2008/0046781 A1 | 2/2008 | Childs et al. |
| 2008/0066179 A1 | 3/2008 | Liu |
| 2008/0066180 A1* | 3/2008 | Repasi ................ G06F 21/563 726/24 |
| 2008/0072326 A1 | 3/2008 | Danford et al. |
| 2008/0077793 A1 | 3/2008 | Tan et al. |
| 2008/0080518 A1 | 4/2008 | Hoeflin et al. |
| 2008/0086720 A1 | 4/2008 | Lekel |
| 2008/0098476 A1 | 4/2008 | Syversen |
| 2008/0120722 A1 | 5/2008 | Sima et al. |
| 2008/0134178 A1 | 6/2008 | Fitzgerald et al. |
| 2008/0134334 A1 | 6/2008 | Kim et al. |
| 2008/0141376 A1 | 6/2008 | Clausen et al. |
| 2008/0184373 A1 | 7/2008 | Traut et al. |
| 2008/0189787 A1 | 8/2008 | Arnold et al. |
| 2008/0201778 A1 | 8/2008 | Guo et al. |
| 2008/0209557 A1 | 8/2008 | Herley et al. |
| 2008/0215742 A1 | 9/2008 | Goldszmidt et al. |
| 2008/0222729 A1 | 9/2008 | Chen et al. |
| 2008/0263665 A1 | 10/2008 | Ma et al. |
| 2008/0295172 A1 | 11/2008 | Bohacek |
| 2008/0301810 A1 | 12/2008 | Lehane et al. |
| 2008/0307524 A1 | 12/2008 | Singh et al. |
| 2008/0313738 A1 | 12/2008 | Enderby |
| 2008/0320594 A1 | 12/2008 | Jiang |
| 2009/0003317 A1 | 1/2009 | Kasralikar et al. |
| 2009/0007100 A1 | 1/2009 | Field et al. |
| 2009/0013408 A1 | 1/2009 | Schipka |
| 2009/0031423 A1 | 1/2009 | Liu et al. |
| 2009/0036111 A1 | 2/2009 | Danford et al. |
| 2009/0037835 A1 | 2/2009 | Goldman |
| 2009/0044024 A1 | 2/2009 | Oberheide et al. |
| 2009/0044274 A1 | 2/2009 | Budko et al. |
| 2009/0064332 A1 | 3/2009 | Porras et al. |
| 2009/0077666 A1 | 3/2009 | Chen et al. |
| 2009/0083369 A1 | 3/2009 | Marmor |
| 2009/0083855 A1 | 3/2009 | Apap et al. |
| 2009/0089879 A1 | 4/2009 | Wang et al. |
| 2009/0094697 A1 | 4/2009 | Provos et al. |
| 2009/0113425 A1 | 4/2009 | Ports et al. |
| 2009/0125976 A1 | 5/2009 | Wassermann et al. |
| 2009/0126015 A1 | 5/2009 | Monastyrsky et al. |
| 2009/0126016 A1 | 5/2009 | Sobko et al. |
| 2009/0133125 A1 | 5/2009 | Choi et al. |
| 2009/0144823 A1 | 6/2009 | Lamastra et al. |
| 2009/0158430 A1 | 6/2009 | Borders |
| 2009/0172815 A1 | 7/2009 | Gu et al. |
| 2009/0187992 A1 | 7/2009 | Poston |
| 2009/0193293 A1 | 7/2009 | Stolfo et al. |
| 2009/0199296 A1 | 8/2009 | Xie et al. |
| 2009/0228233 A1 | 9/2009 | Anderson et al. |
| 2009/0241187 A1 | 9/2009 | Troyansky |
| 2009/0241190 A1 | 9/2009 | Todd et al. |
| 2009/0265692 A1 | 10/2009 | Godefroid et al. |
| 2009/0271867 A1 | 10/2009 | Zhang |
| 2009/0300415 A1 | 12/2009 | Zhang et al. |
| 2009/0300761 A1 | 12/2009 | Park et al. |
| 2009/0328185 A1 | 12/2009 | Berg et al. |
| 2009/0328221 A1 | 12/2009 | Blumfield et al. |
| 2010/0005146 A1 | 1/2010 | Drako et al. |
| 2010/0011205 A1 | 1/2010 | McKenna |
| 2010/0017546 A1 | 1/2010 | Poo et al. |
| 2010/0031353 A1* | 2/2010 | Thomas ............... G06F 11/3604 726/22 |
| 2010/0037314 A1 | 2/2010 | Perdisci et al. |
| 2010/0054278 A1 | 3/2010 | Stolfo et al. |
| 2010/0115621 A1* | 5/2010 | Staniford ............ H04L 63/1416 726/25 |
| 2010/0138919 A1* | 6/2010 | Peng ................. H04L 29/12009 726/22 |
| 2010/0180344 A1 | 7/2010 | Malyshev et al. |
| 2010/0192223 A1 | 7/2010 | Ismael et al. |
| 2010/0220863 A1 | 9/2010 | Dupaquis et al. |
| 2010/0235831 A1 | 9/2010 | Dittmer |
| 2010/0275263 A1* | 10/2010 | Bennett .............. G06F 21/577 726/25 |
| 2010/0281539 A1* | 11/2010 | Burns ................. H04L 63/1441 726/23 |
| 2010/0281541 A1 | 11/2010 | Stolfo et al. |
| 2010/0281542 A1 | 11/2010 | Stolfo et al. |
| 2010/0299754 A1 | 11/2010 | Amit et al. |
| 2010/0306173 A1 | 12/2010 | Frank |
| 2011/0004737 A1 | 1/2011 | Greenebaum |
| 2011/0023115 A1* | 1/2011 | Wright ............... G06F 21/552 726/22 |
| 2011/0023118 A1* | 1/2011 | Wright ............... G06F 11/28 726/23 |
| 2011/0055907 A1 | 3/2011 | Narasimhan et al. |
| 2011/0078794 A1 | 3/2011 | Manni et al. |
| 2011/0093951 A1 | 4/2011 | Aziz |
| 2011/0099620 A1 | 4/2011 | Stavrou et al. |
| 2011/0099633 A1 | 4/2011 | Aziz |
| 2011/0113231 A1 | 5/2011 | Kaminsky |
| 2011/0145918 A1 | 6/2011 | Jung et al. |
| 2011/0145920 A1 | 6/2011 | Mahaffey et al. |
| 2011/0145934 A1 | 6/2011 | Abramovici et al. |
| 2011/0167493 A1 | 7/2011 | Song et al. |

(56) References Cited

U.S. PATENT DOCUMENTS

| | | | |
|---|---|---|---|
| 2011/0167494 A1* | 7/2011 | Bowen | G06F 21/566 726/24 |
| 2011/0173460 A1 | 7/2011 | Ito et al. | |
| 2011/0219449 A1* | 9/2011 | St. Neitzel | G06F 11/00 726/23 |
| 2011/0219450 A1 | 9/2011 | McDougal et al. | |
| 2011/0225624 A1 | 9/2011 | Sawhney et al. | |
| 2011/0225655 A1 | 9/2011 | Niemela et al. | |
| 2011/0247072 A1 | 10/2011 | Staniford et al. | |
| 2011/0265182 A1 | 10/2011 | Peinado et al. | |
| 2011/0289582 A1 | 11/2011 | Kejriwal et al. | |
| 2011/0302587 A1 | 12/2011 | Nishikawa et al. | |
| 2011/0307954 A1 | 12/2011 | Melnik et al. | |
| 2011/0307955 A1 | 12/2011 | Kaplan et al. | |
| 2011/0307956 A1 | 12/2011 | Yermakov et al. | |
| 2011/0314546 A1 | 12/2011 | Aziz et al. | |
| 2011/0320816 A1* | 12/2011 | Yao | G06F 21/316 713/171 |
| 2012/0023593 A1 | 1/2012 | Puder et al. | |
| 2012/0054869 A1 | 3/2012 | Yen et al. | |
| 2012/0066698 A1 | 3/2012 | Yanoo | |
| 2012/0079596 A1 | 3/2012 | Thomas et al. | |
| 2012/0084859 A1 | 4/2012 | Radinsky et al. | |
| 2012/0110667 A1 | 5/2012 | Zubrilin et al. | |
| 2012/0117652 A1 | 5/2012 | Manni et al. | |
| 2012/0121154 A1 | 5/2012 | Xue et al. | |
| 2012/0124426 A1 | 5/2012 | Maybee et al. | |
| 2012/0159519 A1 | 6/2012 | Matsuda | |
| 2012/0174186 A1 | 7/2012 | Aziz et al. | |
| 2012/0174196 A1 | 7/2012 | Bhogavilli et al. | |
| 2012/0174218 A1 | 7/2012 | McCoy et al. | |
| 2012/0198279 A1 | 8/2012 | Schroeder | |
| 2012/0210423 A1 | 8/2012 | Friedrichs et al. | |
| 2012/0222121 A1 | 8/2012 | Staniford et al. | |
| 2012/0255015 A1 | 10/2012 | Sahita et al. | |
| 2012/0255017 A1 | 10/2012 | Sallam | |
| 2012/0260342 A1 | 10/2012 | Dube et al. | |
| 2012/0266244 A1 | 10/2012 | Green et al. | |
| 2012/0278886 A1* | 11/2012 | Luna | G06F 21/552 726/22 |
| 2012/0297489 A1 | 11/2012 | Dequevy | |
| 2012/0330801 A1 | 12/2012 | McDougal et al. | |
| 2012/0331553 A1 | 12/2012 | Aziz et al. | |
| 2013/0014259 A1 | 1/2013 | Gribble et al. | |
| 2013/0019309 A1* | 1/2013 | Strayer | G06N 5/04 726/23 |
| 2013/0036472 A1 | 2/2013 | Aziz | |
| 2013/0047257 A1 | 2/2013 | Aziz | |
| 2013/0074185 A1 | 3/2013 | McDougal et al. | |
| 2013/0086684 A1 | 4/2013 | Mohler | |
| 2013/0097699 A1 | 4/2013 | Balupari et al. | |
| 2013/0097706 A1 | 4/2013 | Titonis et al. | |
| 2013/0111587 A1 | 5/2013 | Goel et al. | |
| 2013/0117852 A1 | 5/2013 | Stute | |
| 2013/0117855 A1 | 5/2013 | Kim et al. | |
| 2013/0139264 A1 | 5/2013 | Brinkley et al. | |
| 2013/0160125 A1 | 6/2013 | Likhachev et al. | |
| 2013/0160127 A1 | 6/2013 | Jeong et al. | |
| 2013/0160130 A1 | 6/2013 | Mendelev et al. | |
| 2013/0160131 A1 | 6/2013 | Madou et al. | |
| 2013/0167236 A1 | 6/2013 | Sick | |
| 2013/0174214 A1 | 7/2013 | Duncan | |
| 2013/0185789 A1 | 7/2013 | Hagiwara et al. | |
| 2013/0185795 A1 | 7/2013 | Winn et al. | |
| 2013/0185798 A1 | 7/2013 | Saunders et al. | |
| 2013/0191915 A1 | 7/2013 | Antonakakis et al. | |
| 2013/0196649 A1 | 8/2013 | Paddon et al. | |
| 2013/0227691 A1 | 8/2013 | Aziz et al. | |
| 2013/0246370 A1 | 9/2013 | Bartram et al. | |
| 2013/0263260 A1 | 10/2013 | Mahaffey et al. | |
| 2013/0291109 A1 | 10/2013 | Staniford et al. | |
| 2013/0298243 A1 | 11/2013 | Kumar et al. | |
| 2014/0013434 A1* | 1/2014 | Ranum | H04L 63/145 726/24 |
| 2014/0053260 A1 | 2/2014 | Gupta et al. | |
| 2014/0053261 A1* | 2/2014 | Gupta | G06F 21/55 726/22 |
| 2014/0090056 A1* | 3/2014 | Manadhata | G06F 21/552 726/23 |
| 2014/0122391 A1 | 5/2014 | Mugan et al. | |
| 2014/0130158 A1 | 5/2014 | Wang et al. | |
| 2014/0137180 A1 | 5/2014 | Lukacs et al. | |
| 2014/0150100 A1* | 5/2014 | Gupta | G06F 21/316 726/22 |
| 2014/0165140 A1* | 6/2014 | Singla | G06F 11/3006 726/1 |
| 2014/0169762 A1 | 6/2014 | Ryu | |
| 2014/0179360 A1 | 6/2014 | Jackson et al. | |
| 2014/0223553 A1* | 8/2014 | Gupta | G06F 21/52 726/22 |
| 2014/0328204 A1 | 11/2014 | Klotsche et al. | |
| 2014/0337836 A1 | 11/2014 | Ismael | |
| 2014/0351935 A1 | 11/2014 | Shao et al. | |
| 2015/0096025 A1 | 4/2015 | Ismael | |
| 2015/0135262 A1* | 5/2015 | Porat | G06F 21/552 726/1 |
| 2015/0172300 A1* | 6/2015 | Cochenour | H04L 63/1425 726/23 |
| 2015/0186645 A1 | 7/2015 | Aziz et al. | |
| 2015/0372980 A1 | 12/2015 | Eyada | |

FOREIGN PATENT DOCUMENTS

| | | |
|---|---|---|
| WO | 02/23805 A2 | 3/2002 |
| WO | 02/006928 A2 | 8/2003 |
| WO | 2007117636 A2 | 10/2007 |
| WO | 2008041950 A2 | 4/2008 |
| WO | 2011084431 A2 | 7/2011 |
| WO | 2011/112348 A1 | 9/2011 |
| WO | 2012/075336 A1 | 6/2012 |
| WO | 2013/067505 A1 | 5/2013 |

OTHER PUBLICATIONS

Apostolopoulos, George; hassapis, Constantinos; "V-eM: A cluster of Virtual Machines for Robust, Detailed, and High-Performance Network Emulation", 14th IEEE International Symposium on Modeling, Analysis, and Simulation of Computer and Telecommunication Systems, Sep. 11-14, 2006, pp. 117-126.

Clark, John, Sylvian Leblanc,and Scott Knight. "Risks associated with usb hardware trojan devices used by insiders." Systems Conference (SysCon), 2011 IEEE International. IEEE, 2011.

FireEye Malware Analysis & Exchange Network, Malware Protection System, FireEye Inc., 2010.

FireEye Malware Analysis, Modern Malware Forensics, FireEye Inc., 2010.

FireEye v.6.0 Security Target, pp. 1-35, Version 1.1, FireEye Inc., May 2011.

Gibler, Clint, et al. AndroidLeaks: automatically detecting potential privacy leaks in android applications on a large scale. Springer Berlin Heidelberg, 2012.

Gregg Keizer: "Microsoft's HoneyMonkeys Show Patching Windows Works", Aug. 8, 2005, XP055143386, Retrieved from the Internet: URL:https://web.archive.org/web/20121022220617/http://www.informationweek- .com/microsofts-honeymonkeys-show-patching-wi/167600716 [retrieved on Sep. 29, 2014].

Heng Yin et al, Panorama: Capturing System-Wide Information Flow for Malware Detection and Analysis, Research Showcase @ CMU, Carnegie Mellon University, 2007.

Idika et al., A-Survey-of-Malware-Detection-Techniques, Feb. 2, 2007, Department of Computer Science, Purdue University.

Isohara, Takamasa, Keisuke Takemori, and Ayumu Kubota. "Kernel-based behavior analysis for android malware detection." Computational intelligence and Security (CIS), 2011 Seventh International Conference on. IEEE, 2011.

Kevin A Roundy et al: "Hybrid Analysis and Control of Malware", Sep. 15, 2010, Recent Advances in Intrusion Detection, Springer Berlin Heidelberg, Berlin, Heidelberg, pp. 317-338, XP019150454 ISBN:978-3-642-15511-6.

(56) References Cited

OTHER PUBLICATIONS

Leading Colleges Select FireEye to Stop Malware-Related Data Breaches, FireEye Inc., 2009.
Li et al., A VMM-Based System Call Interposition Framework for Program Monitoring, Dec. 2010, IEEE 16th International Conference on Parallel and Distributed Systems, pp. 706-711.
Lindorfer, Martina, Clemens Kolbitsch, and Paolo Milani Comparetti. "Detecting environment-sensitive malware." Recent Advances in Intrusion Detection. Springer Berlin Heidelberg, 2011.
Mori, Detecting Unknown Computer Viruses, 2004, Springer-Verlag Berlin Heidelberg.
Oberheide et al., CloudAV.sub.—N-Version Antivirus in the Network Cloud, 17th USENIX Security Symposium USENIX Security '08 Jul. 28-Aug. 1, 2008 San Jose, CA.
Wahid et al., Characterising the Evolution in Scanning Activity of Suspicious Hosts, Oct. 2009, Third International Conference on Network and System Security, pp. 344-350.
Yuhei Kawakoya et al: "Memory behavior-based automatic malware unpacking in stealth debugging environment", Malicious and Unwanted Software (Malware), 2010 5th International Conference on, IEEE, Piscataway, NJ, USA, Oct. 19, 2010, pp. 39-46, XP031833827, ISBN:978-1-4244-8-9353-1.
Zhang et al., The Effects of Threading, Infection Time, and Multiple-Attacker Collaboration on Malware Propagation, Sep. 2009, IEEE 28th International Symposium on Reliable Distributed Systems, pp. 73-82.
U.S. Pat. No. 8,171,553 filed Apr. 20, 2006, Inter Parties Review Decision dated Jul. 10, 2015.
U.S. Pat. No. 8,291,499 filed Mar. 16, 2012, Inter Parties Review Decision dated Jul. 10, 2015.
Venezia, Paul, "NetDetector Captures Intrusions", InfoWorld Issue 27, ("Venezia"), (Jul. 14, 2003).
Whyte, et al., "DNS-Based Detection of Scanning Works in an Enterprise Network", Proceedings of the 12th Annual Network and Distributed System Security Symposium, (Feb. 2005), 15 pages.
Williamson, Matthew M., "Throttling Viruses: Restricting Propagation to Defeat Malicious Mobile Code", ACSAC Conference, Las Vegas, NV, USA, (Dec. 2002), pp. 1-9.
"Network Security: NetDetector—Network Intrusion Forensic System (NIFS) Whitepaper", ("NetDetector Whitepaper"), (2003).
"Packet", Microsoft Computer Dictionary, Microsoft Press, (Mar. 2002), 1 page.
"When Virtual is Better Than Real", IEEEXplore Digital Library, available at, http://ieeexplore.ieee.org/xpl/articleDetails.jsp?reload=true&arnumbe- r=990073, (Dec. 7, 2013).
Abdullah, et al., Visualizing Network Data for Intrusion Detection, 2005 IEEE Workshop on Information Assurance and Security, pp. 100-108.
Adetoye, Adedayo , et al., "Network Intrusion Detection & Response System", ("Adetoye"), (Sep. 2003).
AltaVista Advanced Search Results. "attack vector identifier". Http://www.altavista.com/web/results?Itag=ody&pg=aq& aqmode=aqa=Event+Orch- estrator . . . , (Accessed on Sep. 15, 2009).
AltaVista Advanced Search Results. "Event Orchestrator". Http://www.altavista.com/web/results?Itag=ody&pg=aq& aqmode=aqa=Event+Orch- esrator . . . , (Accessed on Sep. 3, 2009).
Aura, Tuomas, "Scanning electronic documents for personally identifiable information", Proceedings of the 5th ACM workshop on Privacy in electronic society. ACM, 2006.
Baecher, "The Nepenthes Platform: An Efficient Approach to collect Malware", Springer-verlag Berlin Heidelberg, (2006), pp. 165-184.
Baldi, Mario; Risso, Fulvio; "A Framework for Rapid Development and Portable Execution of Packet-Handling Applications", 5th IEEE International Symposium Processing and Information Technology, Dec. 21, 2005, pp. 233-238.
Bayer, et al., "Dynamic Analysis of Malicious Code", J Comput Virol, Springer-Verlag, France., (2006), pp. 67-77.
Boubalos, Chris , "extracting syslog data out of raw pcap dumps, seclists.org, Honeypots mailing list archives", available at http://seclists.org/honeypots/2003/q2/319 ("Boubalos"), (Jun. 5, 2003).
Chaudet, C. , et al., "Optimal Positioning of Active and Passive Monitoring Devices", International Conference on Emerging Networking Experiments and Technologies, Proceedings of the 2005 ACM Conference on Emerging Network Experiment and Technology, CoNEXT '05, Toulousse, France, (Oct. 2005), pp. 71-82.
Chen, P. M. and Noble, B. D., "When Virtual is Better Than Real, Department of Electrical Engineering and Computer Science", University of Michigan ("Chen").
Cisco "Intrusion Prevention for the Cisco ASA 5500-x Series" Data Sheet (2012).
Cisco, Configuring the Catalyst Switched Port Analyzer (SPAN) ("Cisco"), (1992-2003).
Cohen, M.I. , "PyFlag—An advanced network forensic framework", Digital investigation 5, Elsevier, (2008), pp. S112-S120.
Costa, M. , et al., "Vigilante: End-to-End Containment of Internet Worms", SOSP '05, Association for Computing Machinery, Inc., Brighton U.K., (Oct. 23-26, 2005).
Crandall, J.R. , et al., "Minos:Control Data Attack Prevention Orthogonal to Memory Model", 37th International Symposium on Microarchitecture, Portland, Oregon, (Dec. 2004).
Deutsch, P. , "Zlib compressed data format specification version 3.3" RFC 1950, (1996).
Distler, "Malware Analysis: An Introduction", SANS Institute InfoSec Reading Room, SANS Institute, (2007).
Dunlap, George W. , et al., "ReVirt: Enabling Intrusion Analysis through Virtual-Machine Logging and Replay", Proceeding of the 5th Symposium on Operating Systems Design and Implementation, USENIX Association, ("Dunlap"), (Dec. 9, 2002).
Excerpt regarding First Printing Date for Merike Kaeo, Designing Network Security ("Kaeo"), (2005).
Filiol, Eric , et al., "Combinatorial Optimisation of Worm Propagation on an Unknown Network", International Journal of Computer Science 2.2 (2007).
Goel, et al., Reconstructing System State for Intrusion Analysis, Apr. 2008 SIGOPS Operating Systems Review, vol. 42 Issue 3, pp. 21-28.
Hjelmvik, Erik , "Passive Network Security Analysis with NetworkMiner", (IN)Secure, Issue 18, (Oct. 2008), pp. 1-100.
IEEE Xplore Digital Library Sear Results for "detection of unknown computer worms". Http//ieeexplore.ieee.org/searchresult.jsp?SortField=Score&SortOrder=desc- &ResultC . . . , (Accessed on Aug. 28, 2009).
Kaeo, Merike , "Designing Network Security", ("Kaeo"), (Nov. 2003).
Kim, H. , et al., "Autograph: Toward Automated, Distributed Worm Signature Detection", Proceedings of the 13th Usenix Security Symposium (Security 2004), San Diego, (Aug. 2004), pp. 271-286.
King, Samuel T., et al., "Operating System Support for Virtual Machines", ("King").
Krasnyansky, Max , et al., Universal TUN/TAP driver, available at https://www.kernel.org/doc/Documentation/networking/tuntap.txt (2002) ("Krasnyansky").
Kreibich, C. , et al., "Honeycomb-Creating Intrusion Detection Signatures Using Honeypots", 2nd Workshop on Hot Topics in Networks (HotNets-11), Boston, USA, (2003).
Kristoff, J. , "Botnets, Detection and Mitigation: DNS-Based Techniques", NU Security Day, (2005), 23 pages.
Liljenstam, Michael , et al., "Simulating Realistic Network Traffic for Worm Warning System Design and Testing", Institute for Security Technology studies, Dartmouth College ("Liljenstam"), (Oct. 27, 2003).
Lok Kwong et al: "DroidScope: Seamlessly Reconstructing the OS and Dalvik Semantic Views for Dynamic Android Malware Analysis", Aug. 10, 2012, XP055158513, Retrieved from the Internet: URL:https://www.usenix.org/system/files/conference/ usenixsecurity12/sec12- -final107.pdf [retrieved on Dec. 15, 2014].
Marchette, David J., "Computer Intrusion Detection and Network Monitoring: A Statistical Viewpoint", ("Marchette"), (2001).
Margolis, P.E. , "Random House Webster's 'Computer & Internet Dictionary 3rd Edition'", ISBN 0375703519, (Dec. 1998).

(56) References Cited

OTHER PUBLICATIONS

Moore, D., et al., "Internet Quarantine: Requirements for Containing Self-Propagating Code", INFOCOM, vol. 3, (Mar. 30-Apr. 3, 2003), pp. 1901-1910.

Morales, Jose A., et al., ""Analyzing and exploiting network behaviors of malware."", Security and Privacy in Communication Networks. Springer Berlin Heidelberg, 2010. 20-34.

Natvig, Kurt, "SANDBOXII: Internet", Virus Bulletin Conference, ("Natvig"), (Sep. 2002).

NetBIOS Working Group. Protocol Standard for a NetBIOS Service on a TCP/UDP transport: Concepts and Methods. STD 19, RFC 1001, Mar. 1987.

Newsome, J., et al., "Dynamic Taint Analysis for Automatic Detection, Analysis, and Signature Generation of Exploits on Commodity Software", In Proceedings of the 12th Annual Network and Distributed System Security, Symposium (NDSS '05), (Feb. 2005).

Newsome, J., et al., "Polygraph: Automatically Generating Signatures for Polymorphic Worms", In Proceedings of the IEEE Symposium on Security and Privacy, (May 2005).

Nojiri, D., et al., "Cooperation Response Strategies for Large Scale Attack Mitigation", DARPA Information Survivability Conference and Exposition, vol. 1, (Apr. 22-24, 2003), pp. 293-302.

Reiner Sailer, Enriquillo Valdez, Trent Jaeger, Roonald Perez, Leendert van Doom, John Linwood Griffin, Stefan Berger., sHype: Secure Hypervisor Appraoch to Trusted Virtualized Systems (Feb. 2, 2005) ("Sailer").

Silicon Defense, "Worm Containment in the Internal Network", (Mar. 2003), pp. 1-25.

Singh, S., et al., "Automated Worm Fingerprinting", Proceedings of the ACM/USENIX Symposium on Operating System Design and Implementation, San Francisco, California, (Dec. 2004).

Spitzner, Lance, "Honeypots: Tracking Hackers", ("Spizner"), (Sep. 17, 2002).

The Sniffers's Guide to Raw Traffic available at: yuba.stanford.edu/.about.casado/pcap/section1.html, (Jan. 6, 2014).

Thomas H. Ptacek, and Timothy N. Newsham, "Insertion, Evasion, and Denial of Service: Eluding Network Intrusion Detection", Secure Networks, ("Ptacek"), (Jan. 1998).

\* cited by examiner

```
1    <?xml version="1.0" encoding="UTF-8"?>
2    <events>
3     <process mode="started" timestamp="200">
4       <value>c:/documentsandsettings/localsettings/4_m.exe</value>
5       <pid>1810</pid>
6       <ppid>2724</ppid>
7       <parentname>C:\Windows\SysWOW64\cmd.exe</parentname>
8       <filesize>23164</filesize>
9       <md5sum>00b62ddee5376037a1806eac03baa092</md5sum>
10      <sha1sum>7eaf2f73b667157d1a8df4f8a4f7e35f5cbd37ee</sha1sum>
11      <fid ads="">1688849860357625</fid>
12     </process>
13     <apicall timestamp= "300">
14      <processinfo>
15        <pid>1810</pid>
16        <md5>01c32oidk6988035d1836buy06cat365</md5>
17      </processinfo>
18      <dllname>kernel32.dll</dllname>
19      <apiname>WaitForSingleObject</apiname>
20     </apicall>
21     <mutex timestamp= "350">
22      <processinfo>
23        <pid>1810</pid>
24        <md5>00b64dfee5278037a1806fad03baa093</md5>
25      </processinfo>
26     </mutex>
27    </events>
```

*FIG. 4*

```
1   <?xml version="1.0" encoding="UTF-8"?>
2   <events>
3    <nodes>
4     <node id="node_1">
5      <process mode="started" timestamp="200">
6       <value>c:/documentsandsettings/localsettings/4_m.exe<
7   value>
8       <pid>1810</pid>
9       <ppid>2724</ppid>
10      <parentname>C:\Windows\SysWOW64\cmd.exe<
11  parentname>
12      <filesize>23164</filesize>
13      <md5sum>00b62ddee5376037a1806eac03baa092<
14  md5sum>
15      <sha1sum>7eaf2f73b667157d1a8df4f8a4f7e35f5cbd37ee<
16  sha1sum>
17      <fid ads="">1688849860357625</fid>
18     </process>
19    </node>
20    <node id="node_2">
21     <apicall timestamp= "300">
22      <processinfo>
23       <pid>1810</pid>
24       <md5>01c32oidk6988035d1836buy06cat365</md5>
25      </processinfo>
26      <dllname>kernel32.dll</dllname>
27      <apiname>WaitForSingleObject</apiname>
28     </apicall>
29    </node>
30    <node id="node_3">
31     <mutex timestamp= "350">
32      <processinfo>
33       <pid>1810</pid>
34       <md5>00b64dfee5278037a1806fad03baa093</md5>
35      </processinfo>
36     </mutex>
37    </node>
38   </nodes>
39   <edges>
40    <edge id="edge_1">
41     <startnode>node_1</startnode>
42     <endnode>node_2</endnode>
43     <label>calls</label>
44    </edge>
45    <edge id="edge_2">
46     <startnode>node_1</startnode>
47     <endnode>node_3</endnode>
48     <label>creates</label>
49    </edge>
50   </edges>
51  </events>
```

FIG. 5

```
1    <?xml version="1.0" encoding="UTF-8"?>
2    <signature>
3     <rule id="rule_1">
4      <nodes>
5       <node id="node_1">process_1</node>
6       <node id="node_2">registry_1</node>
7      </nodes>
8      <edges>
9       <edge id="edge_1">node_1.created/changed-properties.node_2</edge>
10     </edges>
11    </rule>
12    <rule id="rule_2">
13     <nodes>
14      <node id="node_1">process_1</node>
15      <node id="node_2">file_1</node2>
16     </nodes>
17     <edges>
18      <edge id="edge_1">node_1.opened.node_2</edge>
19     </edges>
20    </rule>
21   </signature>
```

FIG. 11

```
1    <?xml version="1.0" encoding="UTF-8"?>
2    <signature>
3    <nodes>
4       <node id="node_1">Process_3</node>
5       <node id="node_2">Registry_2</node>
6       <node id="node_3">Registry_3</node>
7       <node id="node_4">Registry_4</node>
8       <node id="node_5">Registry_5</node>
9       <node id="node_6">Folder_1</node>
10   </nodes>
11   <edges>
12      <edge id="edge_1">node1.SETVAL.node2</edge>
13      <edge id="edge_2">node1.SETVAL.node3</edge>
14      <edge id="edge_3">node1.SETVAL.node4</edge>
15      <edge id="edge_4">node1.OPEN.node5</edge>
16      <edge id="edge_5">node1.OPEN.node6</edge>
17   </edges>
18   </signature>
```

INTERACTIVE INFECTION VISUALIZATION FOR IMPROVED EXPLOIT DETECTION AND SIGNATURE GENERATION FOR MALWARE AND MALWARE FAMILIES

FIELD

Embodiments of the disclosure relate to the field of cyber security. More specifically, embodiments of the disclosure relate to a system for generating reference models to describe known instances of anomalous, or more specifically, malicious behavior and interactive display screens to illustrate a comparison between incoming data and one or more reference models.

GENERAL BACKGROUND

Over the last decade, malicious software has become a pervasive problem for Internet users as many networked resources include vulnerabilities that are subject to attack. For instance, over the past few years, more and more vulnerabilities are being discovered in software that is loaded onto endpoint devices present on the network, such as vulnerabilities within operating systems for example. These vulnerabilities may be exploited by a person allowing the person to gain access to one or more areas within the network not typically accessible. For example, a person may exploit a vulnerability to gain unauthorized access to email accounts and/or data files.

While some vulnerabilities continue to be addressed through software patches, prior to the release of such software patches, network devices will continue to be targeted for attack by exploits, namely malicious computer code that attempts to acquire sensitive information or adversely influence or attack normal operations of the network device or the entire enterprise network by taking advantage of a vulnerability in computer software.

Currently, a threat detection system observes suspicious or malicious exploits and presents the information regarding the exploits in a list format. While the list format may provide security personnel information directed to uncovered exploits or other detected malicious actions, it fails to identify any relationships between the exploits that would allow security personnel to better understand potential effects, both detected and undetected, caused by the malicious exploit.

In addition, current systems fail to generate reference models based on observed exploits, malicious behaviors, anomalous behaviors (e.g., deviating from typical or expected behavior) or the like for comparison against events observed at a later time.

BRIEF DESCRIPTION OF THE DRAWINGS

Embodiments of the invention are illustrated by way of example and not by way of limitation in the figures of the accompanying drawings, in which like references indicate similar elements and in which:

FIG. 4 is an exemplary portion of data received by the event log engine 230 expressed in eXtensible Markup Language (XML).

FIG. 5 is an exemplary portion of data generated by either the reference model generating logic 215 or the machine learning logic 211 expressed in XML.

FIG. 11 is an exemplary portion of data generated by either the reference model generating logic 215 or the machine learning logic 211 expressed in XML.

FIG. 15 is an exemplary portion of the generated signature (corresponding to the selected section in FIG. 14B) expressed in XML.

DETAILED DESCRIPTION

Figure 1:
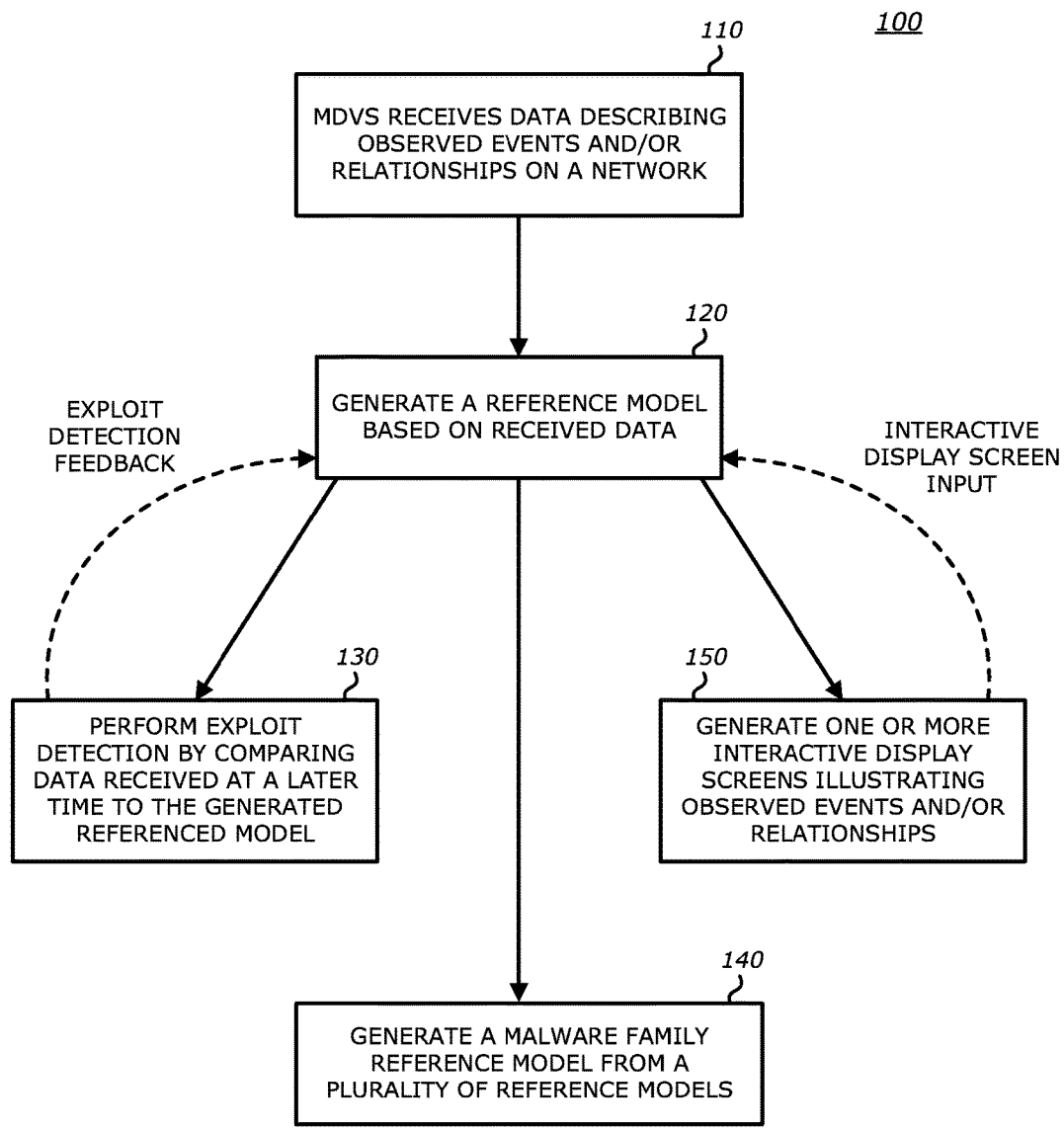
FIG. 1 a flowchart illustrating an exemplary method for generating a reference model and the applications that may be performed by a malware detection and visualization system (MDVS) using the generated reference model.

Various embodiments of the disclosure relate to a malware detection and visualization system that improves exploit detection and/or visual representation of the detection of suspected malware. The malware detection and visualization system includes a machine learning engine that generates reference models used in exploit detection as well as interactive display screen information based on data transmitted to the malware detection and visualization system from one or more endpoint devices, one or more threat detection systems and/or cloud computing services. The generated reference models may be combined to generate malware family reference models allowing the malware detection and visualization system to compare observed events on the network to particularized malware threats in the form of malware affecting a specific file type or malware detected in a common location (e.g., email). Alternatively, a comparison with several reference models or with a large malware family reference model may provide detection against a large range of malware threats. The malware detection and visualization system may take the form of a security appliance or security cloud service, for example. Alternatively, an electronic device may be configured with software, hardware or firmware that includes a malware detection and visualization system. The malware detection and visualization system may be implemented in real-time (e.g., as incoming data is being processed) or as a forensic investigative tool (e.g., after the incoming data has been processed to determine the root cause of a malware exploited has been executed).

The malware detection and visualization system also includes a user interface rendering subsystem that generates interactive display screens from the interactive display screen information and allows security personnel to select displayed malicious events in order to acquire additional information concerning such events as well as generate an alert or a (malware) signature that may be used for subsequent detection of malware associated with these malicious events. The interactive display screens provide a network administrator with a visual representation that compares a reference model of events (e.g., known exploits) and the relationships connecting the events with a group of potentially malicious events and their relationships to one another. The group of potentially malicious events may be derived from observations of endpoint devices, threat detection systems and/or cloud computing services connected to the malware detection and visualization system over a network.

Specifically, in one embodiment, the visual representation allows a viewer to convert a list of events into a nodal diagram in either a top-down representation or a left-to-right representation. The nodal diagrams may enable a view, such as network security personnel, to see how each event relates to one another, if at all. Furthermore, the nodal diagrams provide the visual representation necessary for a viewer to select one or more events, referred to herein as a "grouping" of events, to generate a signature or alert. The signature of a grouping of events may be used as a reference model to check for a particular sequence of events in data received in the future or added to an existing reference model. The alert may be used to notify the network administrator of the observation of a grouping of events that typically implies malicious activity on the network thereby allowing prevention actions to be taken to guard against the malicious activity.

Embodiments of the invention may be employed by or take the form of a network device or apparatus implementing a malware detection and visualization system (MDVS), where the malware detection and visualization system includes a machine learning engine for analyzing data received by the MDVS. The data may include information regarding the observation of events by a server or client device or other system (called an "endpoint"), a threat detection systems (TDS) and/or a cloud computing service. In some embodiments, the observations of events may take place while an endpoint device is operating in real-time or the observations may take place while incoming data is being processed in one or more virtual machines. Examples of incoming data may include, but are not limited or restricted to, network traffic, static files containing structured or unstructured data maintained locally or on a peripheral device and/or executable files. According to one embodiment of the disclosure, an endpoint device, TDS or cloud computing service transmits data regarding an observation of one or more events and/or relationships when an anomalous characteristic of incoming data is observed and thus indicative of an exploit. If so, one or more portions of data may be labeled "suspicious." Throughout the specification, claims and figures, the term "network traffic" will be used in the discussion but any form of incoming data may be substituted.

A TDS may perform static and/or dynamic analyses on incoming data (e.g., network traffic) to determine whether an object of the incoming data is suspicious or malicious. An illustrative example of the static and dynamic analyses is illustrated in the threat detection and prevention (TDP) system in a prior U.S. Patent Application entitled "System, Apparatus and Method for Automatically Verifying Exploits Within Suspect Objects and Highlighting the Display Information Associated with the Verified Exploits," U.S. patent application Ser. No. 14/228,073 filed Mar. 27, 2014, the contents of which are incorporated by reference.

In particular, the machine learning engine may be activated automatically in response to an alert condition that signifies detection of a malicious event by an endpoint device, a TDS and/or a cloud computing service within the network. Alternatively, the machine learning engine may be activated in accordance with a time-based schedule or manually by a user such as security personnel. For instance, the machine learning engine may be activated manually upon selecting a particular visual representation associated with the observance of a malicious event, where one or more events may be concurrently presented on an interactive display screen, and then subsequently selecting a prescribed item on the display screen (e.g., "exploit visualization" button or "timeline visualization" button).

After activation, the machine learning engine may be adapted to obtain received data from a machine learning data store and/or event log, where the received data may include metadata associated with malicious events detected by one or more endpoint devices, TDSes and/or a cloud computing service. The machine learning engine generates a visual representation in the form of a nodal diagram illustrating a potential malware infection, where each node or relationship included in the nodal diagram represents an action, operation, file, process, etc. associated with an anomalous event or relationship. This provides a network administrator with one or more displays directed to the sequence of events to identify which network device(s) and or file(s) within the network may have been infected by the anomalous event. For example, the anomalous event may be an atypical, but non-malicious, operation or relationship; alternatively, the anomalous event may be realized as a malicious event or relationship.

In the nodal diagrams, each event may be selected to display additional information, including, any or all of the following metadata directed to the observance of the selected event: (1) time and date of observance; (2) address information such as the path within the file system in which the affected file is located; (3) process identification of the affected process (if applicable); (4) the particulars of the particular electronic device or cloud computing service that detected the event; and/or (5) the relationship to one or more events associated with the selected event.

I. Terminology

In the following description, certain terminology is used to describe features of the invention. For example, in certain situations, both terms "logic" and "engine" are representative of hardware, firmware and/or software that is configured to perform one or more functions. As hardware, logic (or engine) may include circuitry having data processing or storage functionality. Examples of such circuitry may include, but are not limited or restricted to a microprocessor, one or more processor cores, a programmable gate array, a microcontroller, a controller, an application specific integrated circuit, wireless receiver, transmitter and/or transceiver circuitry, semiconductor memory, or combinatorial logic.

Logic (or engine) may be software in the form of one or more software modules, such as executable code in the form of an executable application, an application programming interface (API), a subroutine, a function, a procedure, an applet, a servlet, a routine, source code, object code, a shared library/dynamic load library, or one or more instructions. These software modules may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; a semiconductor memory; non-persistent storage such as volatile memory (e.g., any type of random access memory "RAM"); persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the executable code is stored in persistent storage.

An "exploit" may be construed broadly as information (e.g., executable code, data, command(s), etc.) that attempts to take advantage of a vulnerability and/or an action by a person gaining unauthorized access to one or more areas of a network, a computer and/or an electronic device. Typically, a "vulnerability" is a coding error or artifact of software (e.g., computer program) that allows an attacker to alter legitimate control flow during processing of the software (computer program) by a network device, and thus, causes the network device to experience undesirable or anomalous behaviors. The undesired or anomalous behaviors may include a communication-based anomaly or an execution-based anomaly, which, for example, could (1) alter the functionality of an network device executing application software in an atypical manner (a file is opened by a first process where the file is configured to be opened by a second process and not the first process); (2) alter the functionality of the network device executing that application software without any malicious intent; and/or (3) provide unwanted functionality which may be generally acceptable in another context. To illustrate, a computer program may be considered as a state machine, where all valid states (and transitions between states) are managed and defined by the program, in which case an exploit may be viewed as seeking to alter one or more of the states (or transitions) from those defined by the program. The term "anomalous behavior" should be understood to include either (i) a first event that is an atypical occurrence or a malicious occurrence, or (ii) a relationship identifying that the first event is based on a second event, the relationship being an atypical relationship between the first and second event or a relationship between the first and second events that is malicious to the network, electronic device on which the relationship appears, or to one or more users of the electronic device or of the network.

According to one embodiment, malware may be construed broadly as computer code that executes an exploit to take advantage of a vulnerability, for example, to harm or co-opt operation of a network device or misappropriate, modify or delete data. Conventionally, malware is often said to be designed with malicious intent.

The term "transmission medium" is a physical or logical communication path between two or more network devices (e.g., any devices with data processing and network connectivity such as, for example, a security appliance, a server, a mainframe, a computer such as a desktop or laptop, netbook, tablet, firewall, smart phone, router, switch, bridge, etc.). For instance, the communication path may include wired and/or wireless segments. Examples of wired and/or wireless segments include electrical wiring, optical fiber, cable, bus trace, or a wireless channel using infrared, radio frequency (RF), or any other wired/wireless signaling mechanism.

The term "network device" should be construed as any electronic device with the capability of connecting to a network. Such a network may be a public network such as the Internet or a private network such as a wireless data telecommunication network, wide area network, a type of local area network (LAN), or a combination of networks. Examples of a network device may include, but are not limited or restricted to, a laptop, a mobile phone, a tablet, a computer, etc.

The term "computerized" generally represents that any corresponding operations are conducted by hardware in combination with software and/or firmware. Also, the terms "compare" or "comparison" generally mean determining if a match (e.g., a certain level of correlation) is achieved between two items where one of the items may include a particular signature pattern.

The term "signature" designates an indicator of a set of characteristics and/or behaviors exhibited by one or more exploits that may not be unique to those exploit(s). Thus, a match of the signature may indicate to some level of probability, often well less than 100%, that a portion of received data constitutes an exploit. In some contexts, those of skill in the art have used the term "signature" as a unique identifier or "fingerprint," for example of a specific virus or virus family (or other exploit), which is generated for instance as a hash of its machine code, and that is a special sub-case for purposes of this disclosure.

The term "observed" indicates that an event or relationship has been detected with a prescribed level of confidence (or probability). A first event or relationship may be observed with a first confidence while a second event or relationship may be observed with a second confidence, the second confidence being lower or higher than the first confidence. Examples of an event may include, but are not limited or restricted to, a process (e.g., an executable file), a non-executable file (e.g., a text document or a registry file), a unique address or location (e.g., a particular website, Internet Protocol (IP) address, or file location).

The term "reference model" should be interpreted as an association of a plurality of events wherein each event is connected to another event and the association includes at least one anomalous behavior (e.g., anomalous event or relationship). For example, a reference model may include a process that (1) injects code into a file unexpectedly and (2) opens multiple files wherein the opening of the files constitutes anomalous behavior. Throughout the specification and claims, the terms "reference model" and "signature" will be used interchangeably.

The term "relationship" means the connection or association of a first event with a second event. Examples of a relationship may include, but are not limited or restricted to, an event: starting a process, terminating a process, modifying a file, generating a file, opening a file, closing a file, deleting a file, infecting a file and/or process, injecting code into file and/or process and/or generating a mutual exclusion (mutex) on a particular file, process, application, etc.

The term "particular" should be interpreted as a characteristic of an event. Examples of particulars include, but are not limited or restricted to, a process identification (PID), a process name, a file name, a process or file path (i.e., unique location on an electronic device), the date and/or time the event was observed and/or occurred, an application programming interface (API) call involved and/or a hash value of the one or more processes or files involved.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

The invention may be utilized for displaying an interactive infection visualization detailing detection, verification and/or prioritization of malicious content. As this invention is susceptible to embodiments of many different forms, it is intended that the present disclosure is to be considered as an example of the principles of the invention and not intended to limit the invention to the specific embodiments shown and described.

II. Malware Detection and Visualization System

Referring to FIG. 1, a flowchart illustrating an exemplary method for generating a reference model and the applications that may be performed by a network device such as, for example, a malware detection and visualization system (MDVS), using the generated reference model is shown. In block 110, the MDVS receives data describing observed events from one or more sources connected to a network. The sources may include one or more endpoint devices, one or more threat detection systems (TDSes) and/or cloud computing services. The received data may provide one or more particulars of the observed events and/or describe relationships between the observed events.

At block 120, the MDVS generates a reference model based on, at least, the received data. The MDVS may use the generated reference to: (i) perform an exploit detection process by comparing data received from one or more sources at a later time to the generated reference model and provide exploit detection feedback to block 120, if applicable (block 130); (ii) generate a malware family reference model from a plurality of generated reference models or reference models received over the network (block 140); and/or (iii) generate one or more interactive display screens to aid in the detection and tracing of exploits and/or one or more anomalous behaviors and provide interactive display screen input to block 120, if applicable (block 150).

Figure 2:
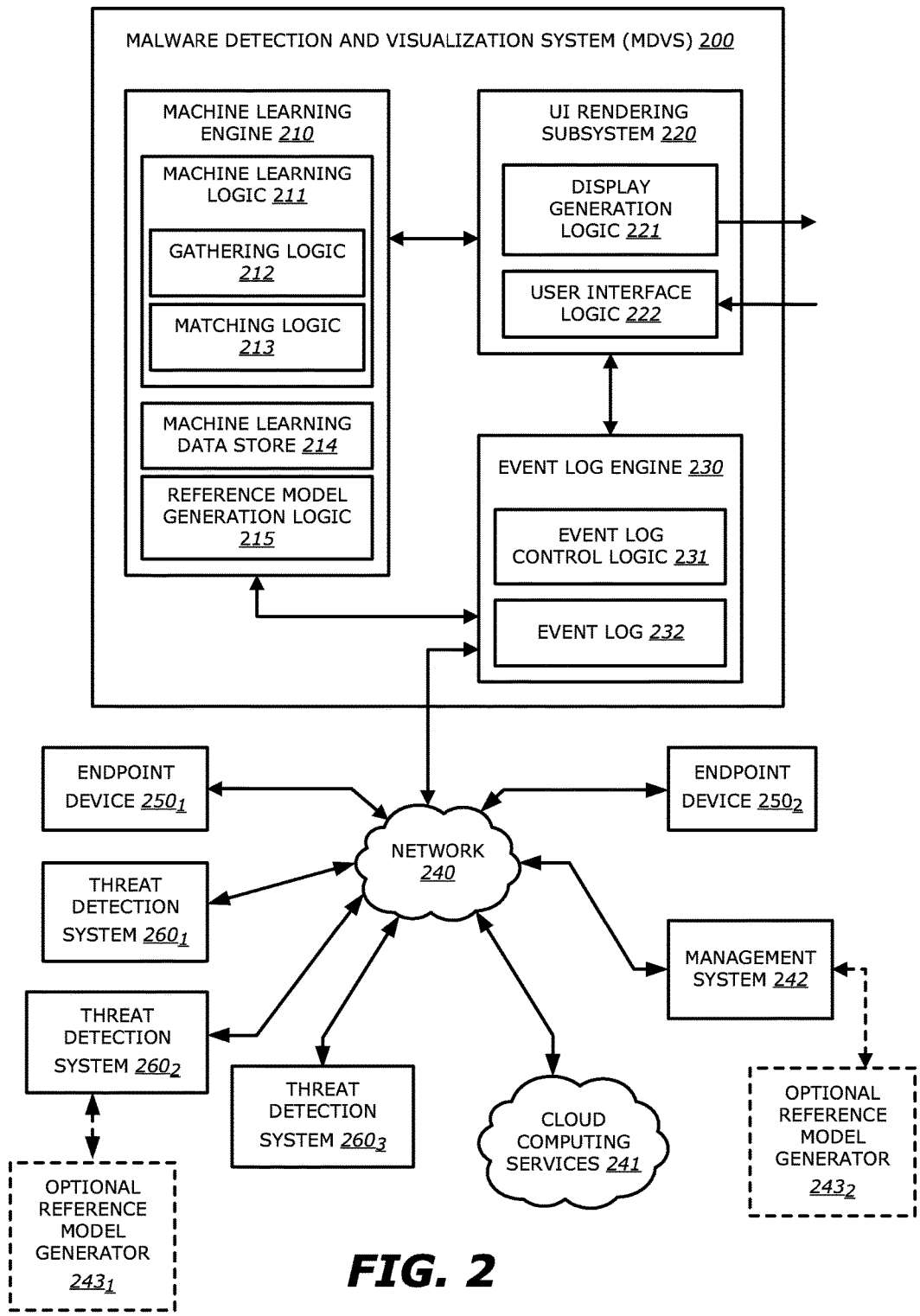
FIG. 2 is a block diagram of an exemplary malware detection and visualization system (MDVS) 200 coupled to a network 240.

Referring to FIG. 2, a block diagram of an exemplary MDVS 200 coupled to a network 240 is shown. The network 240 provides communication connectivity between the MDVS 200 and one or more sources, wherein the sources may include one or more endpoint devices $250_1$-$250_N$ (where N=2 for this embodiment), one or more threat detection systems (TDSes) $260_1$-$260_M$ (where M=3 for this embodiment) and/or the cloud computing services 241. The sources are communicatively coupled to a management system 242, which is adapted to manage the one or more sources as well as the MDVS 200. For instance, the management system 242 may be configured to perform content updates (e.g., upload new rules or modified rules, delete rules, modify parameters that are utilized by the rules, upload metadata stored within other TDSes, or certain metadata associated with the one or more endpoint devices $250_1$ and/or $250_2$) within the one or more endpoint devices $150_1$ and $150_2$ and/or within the one or more TDSes $260_1$-$260_3$.

As shown in FIG. 2, the MDVS 200 is an electronic device that is adapted to analyze information associated with a plurality of events observed at one or more sources (the endpoint devices $250_1$ and $250_2$, the TDSes $260_1$-$260_3$ and/or the cloud computing services 241). The MDVS 200 receives data of the observed events and the particulars of the events over the network 240. The network 240 may include a public network such as the Internet, a private network such as a wireless data telecommunication network, wide area network, a type of local area network (LAN), or a combination of networks.

In general, the endpoint devices $250_1$ and $250_2$ may observe one or more events during operation of the device and transmit a log of the events along with particulars of the events to the MDVS 200. In addition, the TDSes $260_1$-$260_3$ may observe one or more events while processing, for instance in one or more virtual machines, one or more portions of data received over the network 240. The TDSes $260_1$-$260_3$ may then transmit a log containing the events and their particulars to the MDVS 200. The management system 242 controls the transmission of the event logs by the endpoint devices $250_1$ and $250_2$ and/or the TDSes $260_1$-$260_3$. For example, the management system 242 may transmit notifications to the endpoint devices $250_1$ and $250_2$ and/or the TDSes $260_1$-$260_3$ instructing the sources that the event logs should be transmitted to the MDVS 200.

As illustrated in FIG. 2, the MDVS 200 includes a machine learning engine 210, a user interface (UI) rendering subsystem 220 and an event log engine 230. Herein, the machine learning engine 210 may include a machine learning logic 211, a machine learning data store 214, a gathering logic 212, a matching logic 213, and a reference model generation logic 215. The UI rendering subsystem 220 may include a display generation logic 221 and a UI logic 222. The event log engine may include an event log control logic 231 and an event log 232.

In one embodiment, the event log control logic 231 is responsible for receiving data associated with a malicious event that may be detected at and transmitted by the one or more sources over the network 240. Upon receiving the data, the event log control logic 231 may categorize the event and any associated events included in the data, for example, according to the type of event (e.g., executable file, text file, registry file, etc.). The data associated with a malicious event includes the particulars of the malicious event and the particulars of any observed events associated with the malicious event. The event log control logic 231 further adds the particulars of each observed event to the event log 232. Therefore, the MDVS 200 is able to easily access the event particulars in a sorted manner when generating an interactive display screen.

In a second embodiment wherein the MDVS 200 is deployed within an endpoint device $250_1$, the event log control logic 231 is also responsible for observing the events at the endpoint device on which the MDVS 200 is deployed and for adding data associated with an observed malicious event to the event log 232 as well.

The machine learning logic 211 is responsible for analyzing the data associated with the observed events. The gathering logic 212 of the machine learning logic 211 may query the event log 232 to obtain the one or more portions of the data. The matching logic 213 of the machine learning logic 211 may analyze the one or more portions of the data to generate associations of one or more events based on the particulars of the events. For instance, the machine learning logic 211 may realize a first process (e.g., a parent process) launched several secondary processes (e.g., child processes)

and that the child processes subsequently modified one or more files. In addition, the machine learning logic 211 may perform a comparison between the above-referenced realization and one or more reference models formed by events and relationships where one of these events or relationships may be characterized as a known anomalous behavior. Furthermore, the reference model generation logic 215 of the machine learning logic 211 may generate reference models of malware families from the data stored in the event log 232 and data stored in the machine learning data store 214 (the generation of reference models of malware families will be described in detail below). The machine learning logic 211 also generates the interactive display screen information based on the data in the machine learning data store 214 and the event log 232. In one embodiment, the generated reference models of malware families and the interactive display screen information may be expressed in eXtensible Markup Language (XML) and stored in the machine learning data store 214 (as will be discussed below with FIGS. 4 and 5).

The machine learning data store 214 stores the reference models generated by the machine learning logic 211 or received over the network 240 if applicable. For example, an MDVS may be deployed within an endpoint device $250_1$ and/or $250_2$, within one or more TDSes $260_1$-$260_3$, or within the cloud computing services 241. In that such an embodiment, the MDVS 200 may receive one or more reference models generated by the MDVS deployed within the endpoint device $250_1$. The machine learning data store 214 also stores interactive display screens generated by the machine learning logic 211. In the embodiment wherein an MDVS is deployed within the endpoint device $250_1$, the data received over the network may include previously generated reference models and/or interactive display screen information. The MDVS 200 may adopt such data without modification or analyze such data to generate its own reference models and/or interactive display screen data in combination with previously received data.

The display generation logic 221 is responsible for displaying the interactive display screens generated from the interactive display screen information generated by the machine learning logic 211. When a request to display an interactive display screen is received by the MDVS 200, the user interface logic 222 notifies the machine learning logic 211. The machine learning logic 211 then queries the machine learning data store 214 and the event log 232 for the appropriate data (e.g., data pertaining to the relevant event (s)) and generates the interactive display screen information. The machine learning logic 211 may transmit the interactive display screen information to the display generation logic 221 or the display generation logic 221 may query the machine learning data store 214 to obtain the interactive display screen information. Upon obtaining the interactive display screen information, the display generation logic 221 generates the physical display screen that illustrates the association of one or more anomalous events and/or a comparison of one or more reference models of events that constitute known anomalous behaviors with an association of one or more observed events. In some embodiments, the display screen may contain the particulars of the events.

The UI logic 222 is responsible for receiving requests for the generation of an interactive display screen, requests to display particulars of an event and/or requests to generate signatures (e.g., reference models).

FIG. 2 also illustrates optional reference model generators $243_1$-$243_2$ attached to sources connected to the network 240. The reference model generator $243_1$ may be connected to (or part of) the TDS $260_2$. The reference model generator $243_1$ may generate one or more reference models based on network traffic analyzed by the TDS $260_2$. The one or more reference models may be transmitted to the MDVS 200 through the network 240 and stored in either the event log 232 or the machine learning data store 214. Similarly, the reference model generator $243_2$ may generate reference models based on data supplied to the management system from a network administrator and/or one or more sources, for example, the endpoint devices $250_1$ and/or $250_2$, one or more TDSes $260_1$-$260_3$ and/or the cloud computing services 241. The generated reference models may be transmitted to the MDVS 200 through the network 240 and stored in either the event log 232 or the machine learning data store 214.

Figure 3:
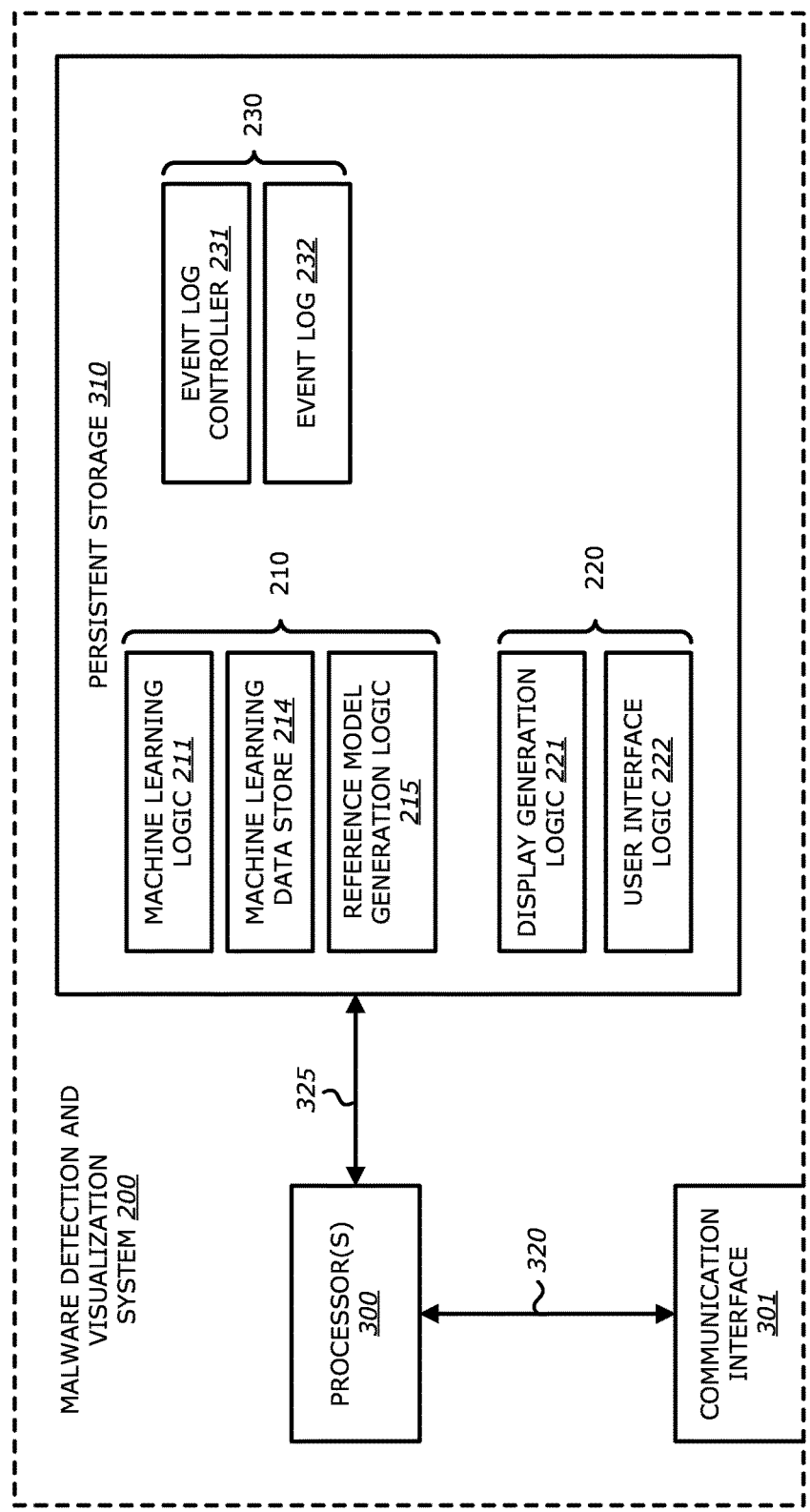
FIG. 3 is an exemplary embodiment of a logical representation of the MDVS of FIG. 2.

Referring to FIG. 3, an exemplary embodiment of a logical representation of the MDVS of FIG. 2 is shown. The MDVS 200 includes one or more processors 300 that are coupled to communication interface logic 301 via a first transmission medium 320. Communication interface 301 enables communications with endpoint devices $250_1$ and/or $250_2$, one or more TDSes $260_1$-$260_3$, the cloud computing services 241 and/or the management system 242 of FIG. 2. According to one embodiment, communication interface 301 may be implemented as a physical interface including one or more ports for wired connectors. Additionally, or in the alternative, communication interface logic 301 may be implemented with one or more radio units for supporting wireless communications with other electronic devices.

The processor(s) 300 is further coupled to the persistent storage 310 via transmission medium 325. According to one embodiment of the disclosure, persistent storage 310 may include (a) the machine learning engine 210, including the machine learning logic 211 and/or the machine learning data store 214; (b) the UI rendering subsystem 220 that includes the display generation logic 221 and the UI logic 222; and (c) the event log engine 230 including the event log control logic 231 and the event log 232. Of course, when implemented as hardware, one or more of these logic units could be implemented separately from each other.

III. Reference Model Generation

Referring to FIG. 4, an exemplary portion of data received by the event log engine 230 expressed in XML is shown. As described above, the event log control logic 231 receives data transmitted by the one or more sources over the network 240 pertaining to one or more events and the particulars of the events. FIG. 4 illustrates one embodiment of data of events and particulars of the events received by the event log control logic 231. The data illustrated in FIG. 4 is stored in the event log 232 until it is gathered by the gathering logic 212 (discussed below).

FIG. 4 illustrates details of a first event observed at a time having a timestamp of "200." For example, lines 3-12 state one or more attributes of the process information of a first event at a time having a timestamp value of "200" detailing: (1) the value of the event ("<value>"); (2) the process identification of the event ("<pid>"); (3) the parent process identification of the event ("<ppid>"); (4) the parent name of the event ("<parentname>"); (5) the file size of the event ("<filesize>"); (6) the hash value (e.g., a particular message digest (MD5) hash value) of the event ("<md5sum>"); (7) the securer hash algorithm (SHA) value of the event ("<sha1sum>"); and (1) the file identification of the event ("<fid>"). Similarly, lines 13-20 and 21-26 recite event particulars of a second and third event at times having timestamp values of "300" and "350," respectively.

Based on the data illustrated in FIG. 4, a reference model may be generated by the reference model generation logic 215 of FIG. 2. The generation of a reference model may be triggered, for example, at predetermined time intervals, after receipt of a predetermined amount of data from the network 240, and/or manually by a system administrator or the like. Upon the triggering of the generation of a reference model the gathering logic 212 gathers the data illustrated in FIG. 4 and passes the data to the reference model generation logic 215. Alternatively, the data illustrated in FIG. 4 may be gathered by the gathering logic 212 and passed to the machine learning logic 211 which will generate an association of potentially malicious events for the matching logic 213 to use in an exploit detection process (discussed below).

Referring to FIG. 5, an exemplary portion of data generated by either the reference model generating logic 215 or the machine learning logic 211 expressed in XML is shown. As mentioned above, the gathering logic 212 gathers the data illustrated in FIG. 4 and may pass the data to the reference model generating logic 215. The reference model generating logic 215 generates a reference model for use in an exploit detection process. The generated reference model may be expressed in XML as illustrated in FIG. 5 and subsequently stored in the machine learning data store 214. Alternatively, FIG. 5 may represent an association of potentially malicious events that will be used by the matching logic 213 in an exploit detection process, such as the exploit detection process performed by the matching logic 213 illustrated in FIGS. 6-7C.

The modifications to the data as illustrated in FIG. 4 to obtain the data as illustrated in FIG. 5 provide indicators of the beginning and end of event data (e.g., "<nodes>") as well as the relationship (e.g., "<edge>") between two events. The modifications may be performed by either the reference model generation logic 215 or the machine learning logic 211.

IV. Applications of Reference Model(s)

A. Improved Exploit Detection

Figure 6:
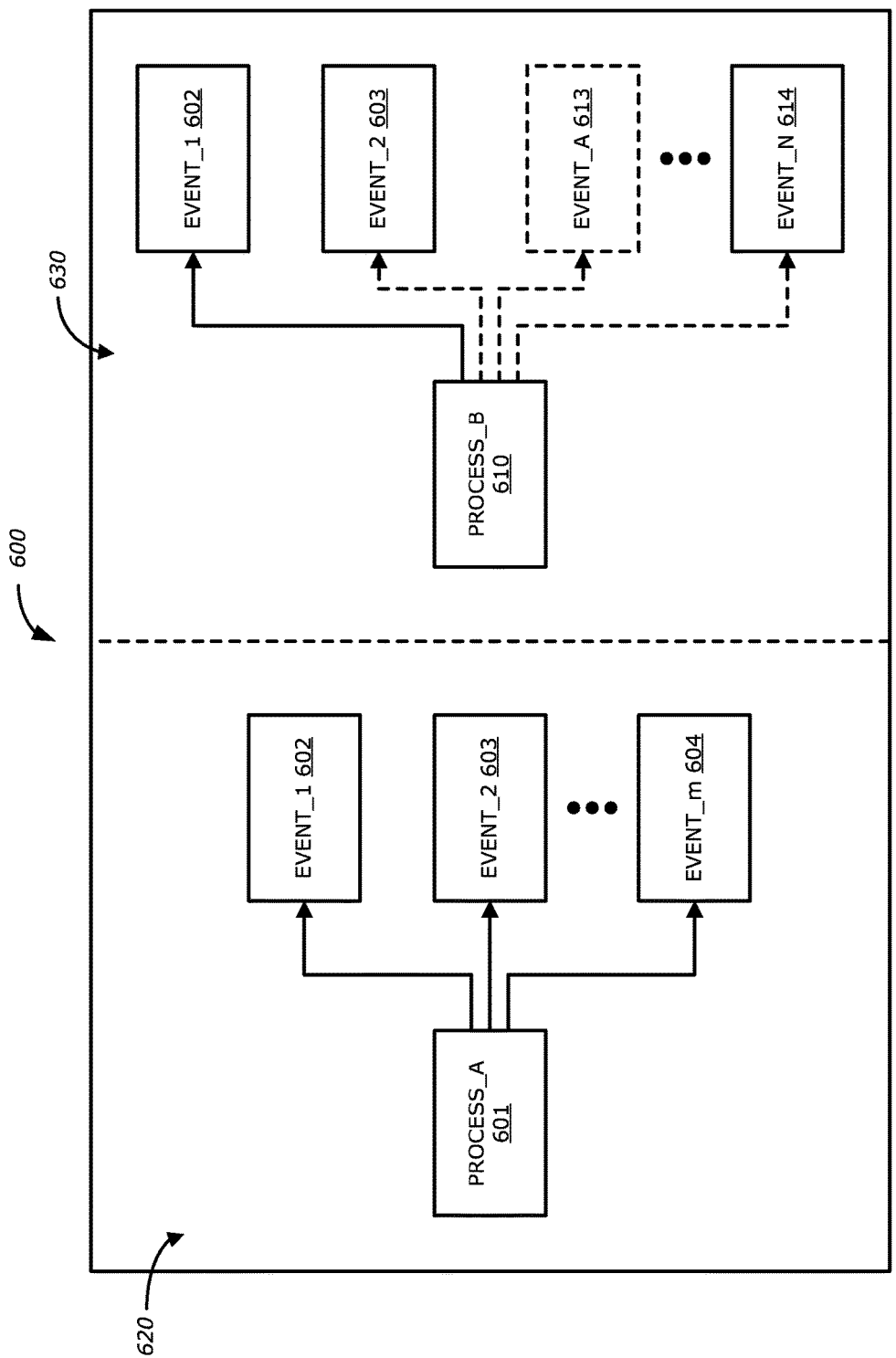
FIG. 6 is an exemplary illustration of a comparison of a reference model of an association of known malicious events with an association of potentially malicious observed events.

Referring now to FIG. 6, an exemplary illustration of a comparison of a reference model of an association of known malicious events with an association of potentially malicious observed events is shown. The machine learning logic 211 may perform an exploit detection process by performing the comparison illustrated in FIG. 6. The exploit detection process may be triggered, for example, at predetermined time intervals, after receipt of a predetermined amount of data from the network 240, and/or manually by a system administrator or the like.

The determination of selecting which reference model(s) to use in a comparison such as that illustrated in FIG. 6 is based on one or more factors. Examples of factors include, but are not limited or restricted to, the infection type of one or more events included in the received data (the association of potentially malicious observed events), the type of a file included in the received data and/or the most commonly matched reference models. Alternatively, the received data may be compared to all of the reference models.

Upon the triggering of the exploit detection process, the gathering logic 212 of the machine learning logic 211 initially gathers the data received over the network 240 and stored in the event log 232. The gathering logic 212 also gathers the one or more reference models that will be used in the comparison. The matching logic 213 of the machine learning logic 211 compares the received data and the one or more reference models gathered by the gathering logic 212.

In FIG. 6, the interactive display screen 600 illustrates a side-by-side comparison of two nodal diagrams; the left side being the reference model 620 and the right side being an association of observed potentially malicious events 630 ("the association 630"). The reference model 620 represents an association of known or observed events and the relationships between the events. The observations or knowledge is such that the event and/or relationship was observed and/or known to have occurred with at least a certain probability. The reference model generation logic 215 of FIG. 2 may generate reference models such as reference model 620 from one or more of the data stored in the machine learning data store 214, the data stored in the event log 232 and/or data received over the network 240.

The events Event_1 602, and Event_2 603 through Event_m 604 were observed as a result of the performance of an action or operation caused by the Process_A 601. The events appearing in the reference model 620 are present as a result of one or more events or relationships being deemed at least anomalous, where one or more events or relationships may have been deemed malicious. In one embodiment, the Process_A 601 may have been deemed malicious by the $TDS\ 260_1$ of FIG. 2 and such information transmitted to the MDVS 200. In some embodiments, all behaviors caused by one malicious event may be considered malicious while in other embodiments, only a subset of the events caused by a malicious event may be deemed malicious.

Referring to the association 630, the solid lines appearing in the association 630 signify that the events and/or relationships (i.e., the line connecting two events) were observed with at least a first confidence (e.g., observation that the event occurred or existed exceeds a first predetermined probability threshold). The dotted lines appearing in the association 630 signify that the events and/or relationships were observed with a second confidence, wherein the second confidence is different and less than the first confidence.

In the comparison performed by the matching logic 213 as illustrated in FIG. 6, some events and/or relationships may be equivalent in both the reference model 620 and the association 630. As is illustrated, the events Event_1 602 and Event_2 603 appear in both the reference model 620 and the association 630. In addition, the machine learning logic 211 may infer that one or more events and/or relationships were observed and should be included in the association 630 based on the reference model 620. For example, the machine learning logic 211 may "learn" that when two events are observed, a third typically is as well and therefore infer that the third event was observed, adding it to association 630. The concept of the machine learning logic 211 learning when events and/or relationship are likely to have be observed by recognizing trends and patterns based on the data stored in the machine learning data store 214, stored in the event log 232 and/or received over the network 240 will be explained in detail along with the discussion of FIGS. 7A-7C below.

Figure 7A:
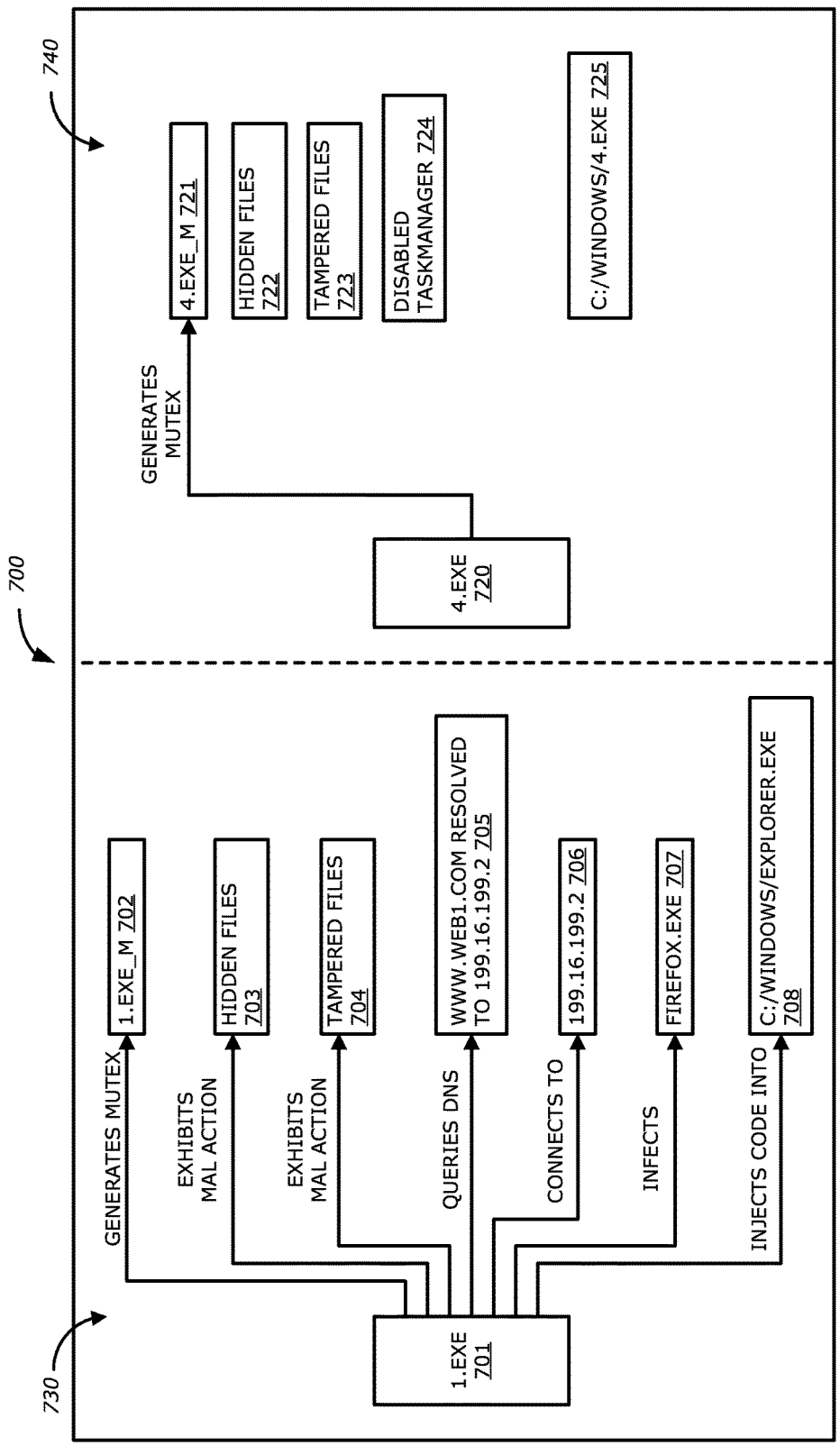
FIGS. 7A-7D are exemplary diagrams illustrating the exploit detection process performed by the matching logic 213 comparing an association of potentially malicious observed events with a reference model of known malicious events.
Figure 7B:
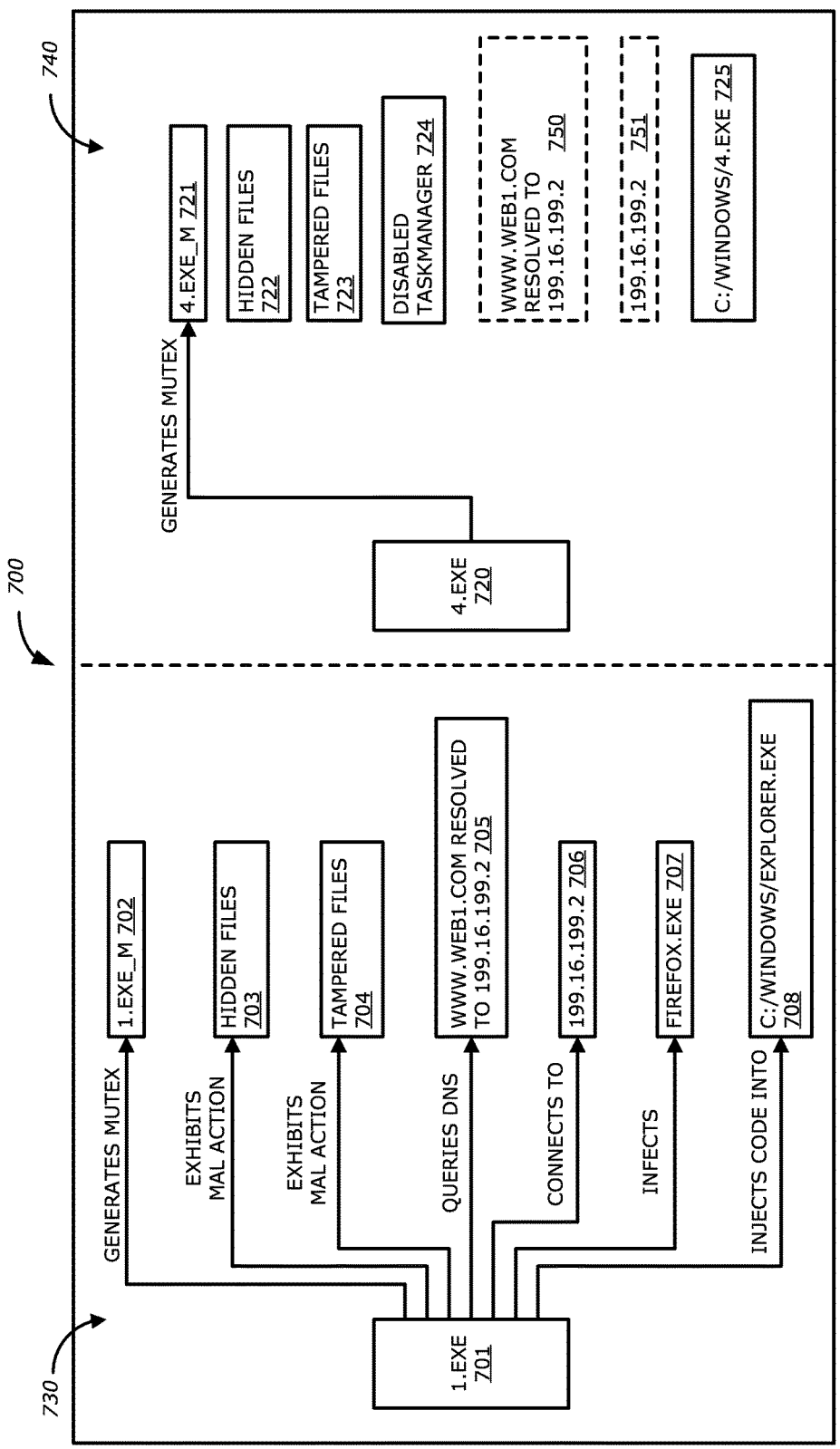
Figure 7C:
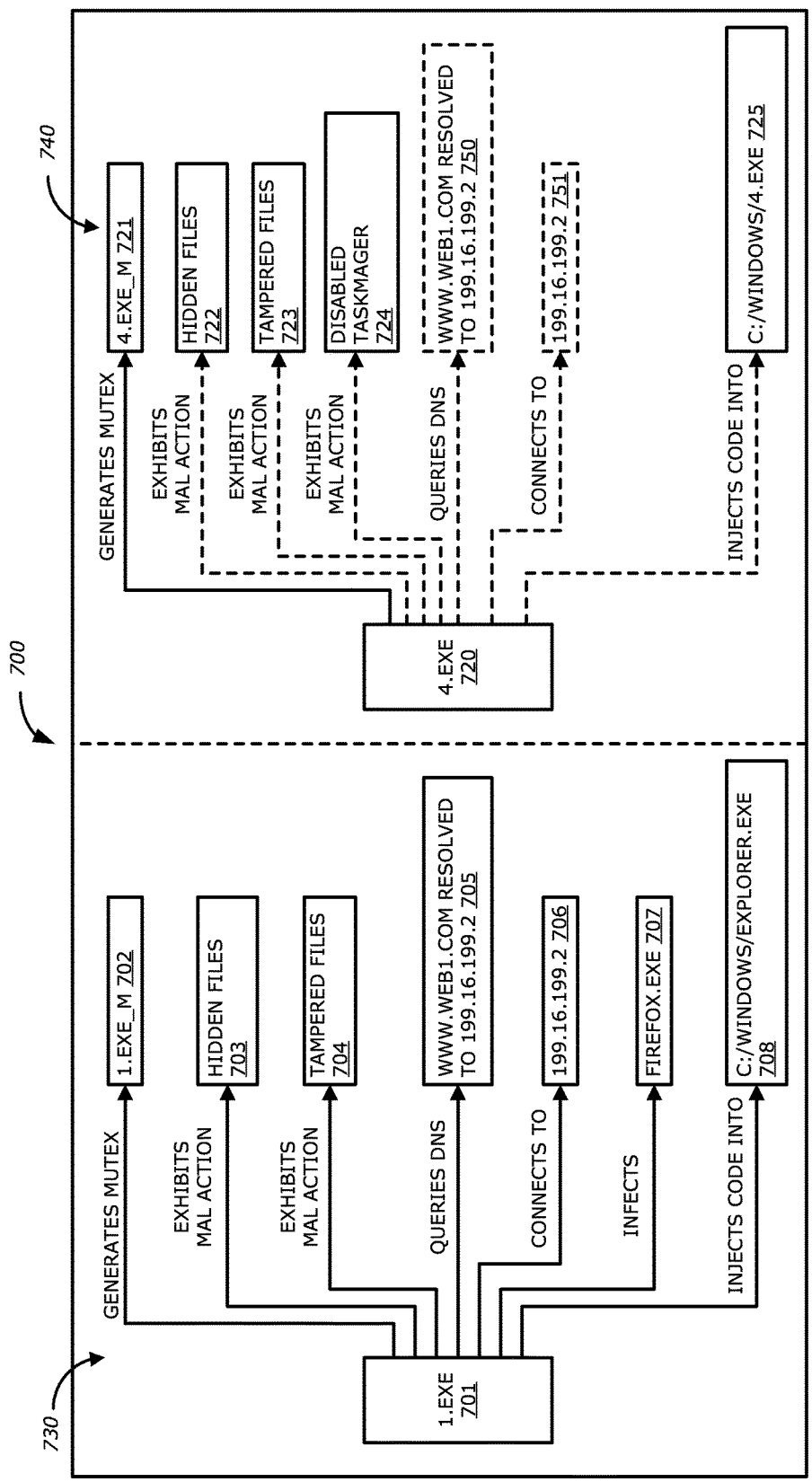

Referring to FIGS. 7A-7D, exemplary diagrams illustrating the exploit detection process performed by the matching logic 213 comparing an association of potentially malicious observed events with a reference model of known malicious events are shown. The changes seen between FIG. 7A to FIG. 7B and from FIG. 7B to FIG. 7C illustrate one embodiment of a process the machine learning logic 211 may perform to determine whether at least a portion of the association of potentially malicious observed events matches with one or more reference models. In one embodiment, the progression from FIG. 7A to FIG. 7B to FIG. 7C may be considered the development of one interactive display screen. Alternatively, FIGS. 7A-7C may be considered separate interactive display screens providing a viewer three different perspectives of the potentially malicious events and/or relationships included within the association of potentially malicious events (the right side of the interactive display screen). The embodiment in which FIGS. 7A-7C may be interactive display screens will be discussed below.

The following discussion of FIGS. 7A-7C will explain an embodiment wherein the three figures illustrate the exploit detection process performed by the machine learning logic 211. In addition, the discussion of the changes seen from FIG. 7C to FIG. 7D will explain the enhancement of a reference model based on the data transmitted to the MDVS 200.

Referring to FIG. 7A, an initial stage of the exploit detection process is shown. The exploit detection process includes a comparison 700 that includes the reference model 730 and the association of potentially malicious events 740 ("the association 740"). The reference model 730 includes the event 1.exe 701 that is seen to cause the performance of an action or operation in the events 1_M.exe 702, "hidden files" 703, "tampered files" 704, "www.web1.com resolved to 199.16.199.2" 705, "199.16.199.2" 706, firefox.exe 707 and C:/Windows/explorer.exe 708.

In addition, the reference model 730 details the relationships between the events. For example, FIG. 7A provides that the event 1.exe 701 caused the creation of a mutex to be performed that resulted in the observation of the event 1.exe_M 702. Likewise, it is seen that the event 1.exe 701 exhibited malicious action that resulted in various hidden files 703. Similarly, the relationships between the event 1.exe 701 and the other events included in the reference model 730 are illustrated in the comparison 700.

The association 740 includes the event 1.exe 701 that is seen to cause the performance of an action or operation resulting in the events 1_M.exe 721, "hidden files" 722, "tampered files" 723, "disabled taskmanager" 724 and C:/Windows/4.exe 725. In contrast to the reference model 730, not all of the relationships between the events included in the association 740 are illustrated in FIG. 7A. The association 740 shown in FIG. 7A may not include enough data for the MDVS 200 to initially recognize all events and relationships with at least a first confidence, as mentioned above. As illustrated in FIG. 7A, the machine learning logic 211 may not initially have access to data allowing the machine learning logic 211 to determine relationships between the event 720 and the events 722, 723 and 725 with at least the first confidence.

Therefore, as one embodiment, FIG. 7A illustrates the first stage in the process of generating the association 740 that is shown in FIG. 7C. For example, the data used to generate the association of FIG. 7A may have been transmitted to the MDVS 200 from the TDS 260₁. The TDS 260₁ may have, for example, processed a portion of network traffic it received in one or more virtual machines and observed, among others, the events and relationship included in the association 740 of FIG. 7A. One or more of the events and/or relationships included in the association 740 of FIG. 7A may be been deemed malicious, prompting the TDS 260₁ to transmit the observations to the MDVS 200.

Referring to FIG. 7B, a second stage of the exploit detection process is shown. The association 740 illustrated in FIG. 7B is seen to have two additional events included compared to the association 740 of FIG. 7A. In particular, the two events, "www.web1.com resolves to 199.16.199.2" 750 and "199.16.199.2" 751, are illustrated using dotted lines. In the embodiment of FIGS. 7A-7C, dotted lines are intended to represent that the events and/or relationships were observed with a second confidence, meaning that the data available to the machine learning logic 211 did not provide as much support for the occurrence or existence of the events illustrated using dotted lines as the data did for the occurrence or existence of the events illustrated using solid lines.

Alternatively, the dotted lines may represent that the event was not detected at any one source but instead is an inference from the event's appearance in the reference model 730. For example, the dotted box surrounding the "www.web1.com resolves to 199.16.199.2" event 750 may represent that no source connected to the MDVS 200 via the network 240 observed the "www.web1.com resolves to 199.16.199.2" event 750. Instead, based on the similarities between the association 740 and the reference model 730, the matching logic 213 inferred that the "www.web1.com resolves to 199.16.199.2" event 750 should be included and may have occurred but its observance did not occur.

In one embodiment, the data may have only provided one source of evidence of the occurrence of existence of the events illustrated using dotted lines whereas the first confidence requires Y or more sources of evidence are state that an event occurred or existed (wherein Y≥2). Alternatively, or in addition, the dotted lines may represent that the machine learning logic 211 has inferred that the events illustrated using dotted lines occurred or existed. Through machine learning, the machine learning logic 211 may have recognized that the events illustrated using dotted lines typically occur or exist when one or more of the events illustrated using solid lines were observed and therefore infer that it is likely the events illustrated dotted lines occurred or existed but were not observed with the first confidence. For example, the machine learning logic 211 may recognize that when an executable file (e.g., 4.exe 720) generates a mutex which is followed by the hiding of files and tampering with network settings, it is likely that the website "www.web1.com" resolves to the IP address "199.16.199.2" and source (e.g., TDP 260₁) connected to the IP address "199.16.199.2" based on the reference model 730.

Referring to FIG. 7C, the association 740 is fully illustrated such that the relationships between the event 4.exe 720 and the events 1_M.exe 721, "hidden files" 722, "tampered files" 723, "disabled taskmanager" 724, "www.web1.com resolved to 208.73.211.247" 750, "208.73.211.247" 751 and C:/Windows/4.exe 725 are present in the comparison 700. As was discussed regarding FIG. 7B, the machine learning logic 211 may infer one or more relationships based on at least a comparison 700 of the association 740 with the reference model 730. Therefore, the comparison 700 as illustrated in FIG. 7C provides the matching logic 213 the association of the event 4.exe 720 with the events 721-725, 750 and 751 allowing the matching logic 213 to make a determination as to whether the association 740 matches with the reference model 730.

Based on FIGS. 7A-7C, the matching logic 213 may ascertain what malicious events occurred or existed, the relationships between the one or more events as well as the confidence of the machine learning logic 211 of the occurrence or existence of a particular event and/or relationship. The comparison 700 in FIGS. 7A-7C performed by the matching logic 213 to compare the association of observed and/or inferred events with a reference model allowing the matching logic 213 to determine the extent of malicious activity that may have occurred and what files, processes, locations, etc. may have been affected.

Furthermore, the matching logic 213 may determine whether a correlation exists between the reference model 730 and the association 740 depending on predetermined characteristics and thresholds. For example, the matching logic 213 may find a correlation when Z specific events are found to match in the reference model 730 and the association 740 (wherein Z is a predetermined number). Alternatively, the matching logic 213 may determine a correlation exists if a predetermined number of events and/or relationships are found to match between the reference model 730 and the association 740. In yet another embodiment, the matching logic 213 may find a correlation if a predetermined number of events and/or relationships are found to match and one or more events and/or relationships are not present in both of the reference model 730 and the association 740. Any combination of the above scenarios may be used to determine whether a correlation is present between the reference model 730 and the association 740. The machine learning logic 211 may store these correlations in the machine learning data store 211 as a way of "learning" when one or more malicious events and/or relationships may be inferred.

Figure 7D:
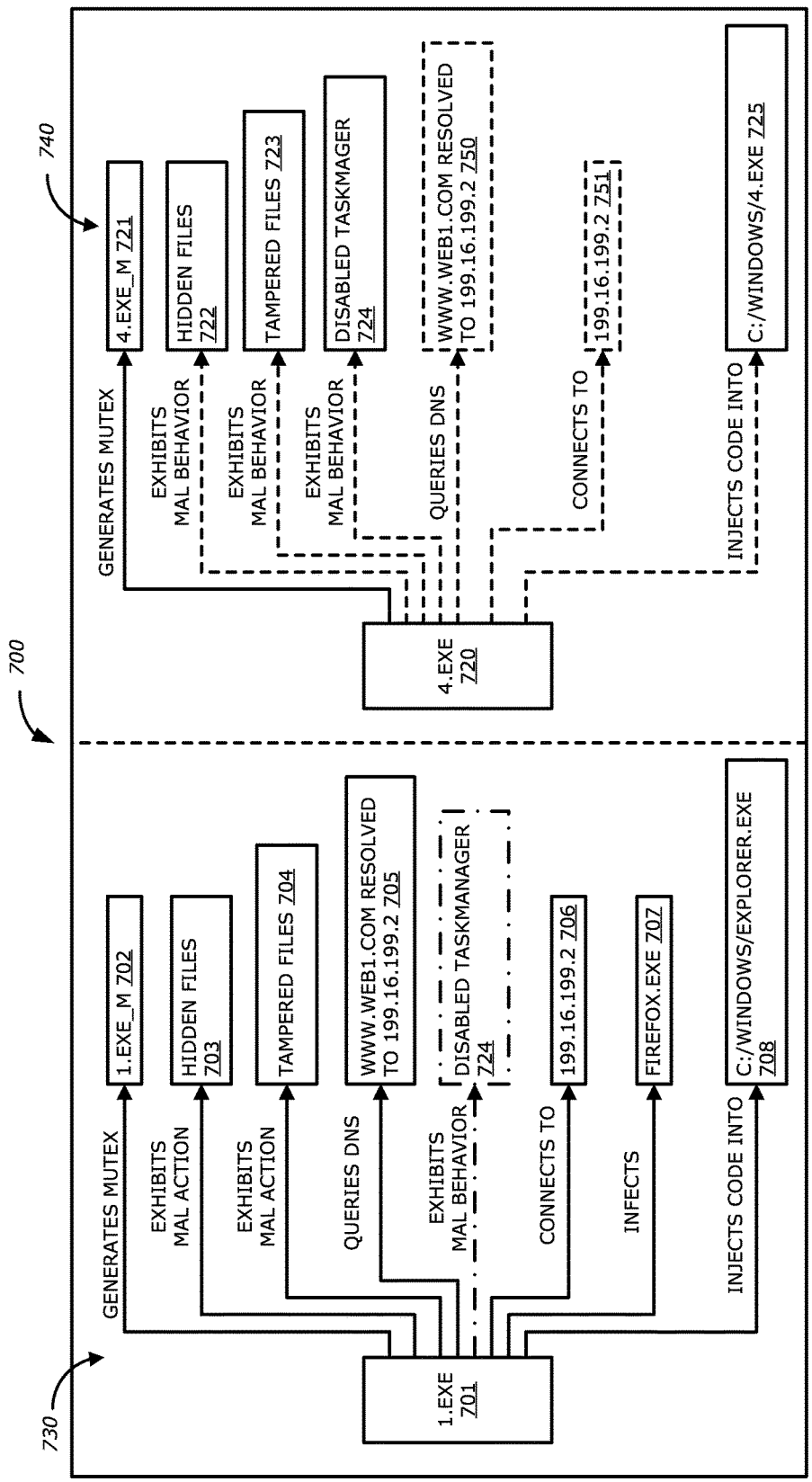

Referring to FIG. 7D, an enhancement to the reference model 730 is shown. The event "Disabled TaskManager 724" has been added to the reference model 730 and is illustrated with a dotted and dashed line. In addition, the relationship between the process 1.exe 701 and the event "Disabled TaskManager 724" is also present in the reference model 730 similarly illustrated with a dotted and dashed line. As a result of the data transmitted to the MDVS 200, and optionally, in addition to the data stored in the event log 232 and/or the machine learning data store 212, the machine learning logic 211 may determine that there is sufficient correlation between an event and/or relationship and a reference model such that the event and/or relationship should be added to the reference model.

In one embodiment, a "sufficient correlation" may include the event and/or relationship appearing within a grouping of events a predetermined number of times. For example, if the event "Disabled TaskManager 724" appears X number of times (wherein X is a predetermined threshold) when a process (e.g., 4.exe 720) generates a mutex, hides files and tampers with network settings, the event "Disabled TaskManager" 724 will be added to the reference model including those events. Referring back to FIG. 1, the addition of event "Disabled TaskManager 724" and the relationship between the between the process 1.exe 701 and the event "Disabled TaskManager 724" is illustrated in FIG. 1 as "exploit detection feedback" from block 130 to block 120. The addition of one or more events and/or relationships to a reference model constitutes exploit detection feedback as illustrated in FIG. 1. The one or more events and/or relationships determined by the matching logic 213 and/or the machine learning logic 211 to be added to one or more reference models may be transmitted to the reference model generation logic 215. The gathering logic 212 may gather the reference models to be updated from the machine learning data store 214. The reference model generation logic 215 may then perform an updating process to the one or more gathered reference models by adding the one or more events or relationships into the one or more reference models. The reference models that are to be updated may be determined by gathering all reference models having one or more common events and/or relationships with the reference model used in the comparison or all reference models included in the machine learning data store 214. Alternatively, reference models to be updated may be selected based on file types included in the reference models and/or a source that observed the events included in the reference models (e.g., email TDS, web TDS, file TDS and/or mobile TDS).

The enhanced reference model 730 may be used to update and/or allow for more particularized exploit detection. For example, the enhanced reference model 730 may be used by, among others, the management system 242 to further configure or reconfigure one or more of the sources (e.g., the endpoint device $250_1$ and/or the TDS $260_1$). The reconfiguration or further configuration may entail, for example, configuring the one or more sources to search one or more pieces of network traffic for an extended amount of time, search the one or more pieces of network traffic multiple times and/or search for different malware exploits and/or certain events and/or relationships.

Alternatively, or in addition to, the enhanced reference model 730 may provide a means for updating one or more correlation rules for classifying malware (e.g., updating signatures or rules for determining whether an object of network traffic is suspicious and/or configuring and/or reconfiguring one or more virtual machines (VMs) included in one or more sources). Such updated signatures may be more robust due to the more complete picture of a malware exploit the updated signature provides. In one embodiment, the enhanced reference model 730 may provide improved alerts and recognition of malware based on the enhancement.

Figure 8:
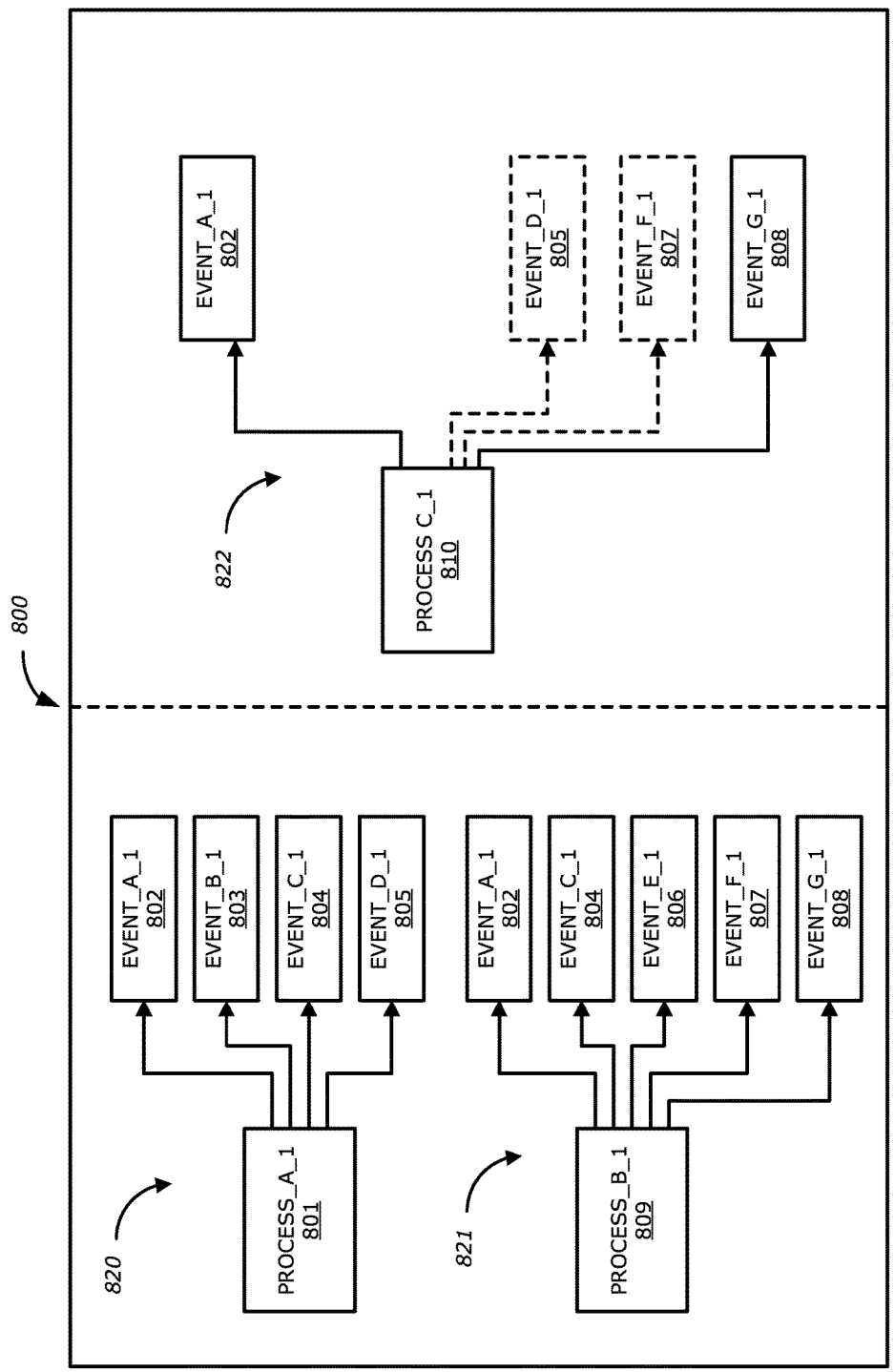
FIG. 8 is an exemplary illustration of a comparison 800 of reference models 820 and 821 with an association of potentially malicious observed events.

Referring to FIG. 8, an exemplary illustration of a comparison 800 of reference models 820 and 821 with an association of potentially malicious observed events is shown. Similar to FIGS. 7A-7C, the comparison 800 includes a left side and a right side. However, in contrast to FIGS. 7A-7C showing a single reference model, the left side of the comparison 800 includes the reference model 820 and the reference model 821. One embodiment of the generation process of the association of potentially malicious events 822 (the association 822) is similar to the embodiment describing FIGS. 7A-7C. Furthermore, in the embodiment of FIG. 8, the machine learning logic 211 may infer events and/or relationships from two reference models.

In FIG. 8, the association 822 is seen to have solid lines illustrating the Event_A_1 802 and the Event_G_1 805. In addition, the relationship connecting the Process_C_1 810 with the Event_A_1 802 and Event_G_1 808 are illustrated using solids lines. Therefore, FIG. 8, illustrates the Event_A_1 802 and the Event_G_1 808 and the connections (i.e., relationships) between the Process_C_1 810 and the events Event_A_1 802 and Event_G_1 808 were observed with at least a first confidence by one or more of the sources connected to, for example, the network 240 of FIG. 2.

Furthermore, the events Event_D_1 805 and Event_F_1 807 as well as the connections between the Process_C_1 810 and the events Event_D_1 805 and Event_F_1 807 are illustrated as dotted lines meaning these events and connections were inferred from the Process_A_1 801 and/or the Process_B_1 809. As can be seen in FIG. 8, the reference model 820 includes the Event_D_1 805. The reference model 821 includes the Event_F_1 807. In addition, not all events present in one or more of the reference models need to be inferred as occurring within the received data. For example, the events Event_B_1 803 and Event_C_1 804 was not inferred by the machine learning logic 211 as having occurred with the association 822. In one embodiment, the received data along with the reference models available to the machine learning logic 211 may not have supported such an inference.

B. Malware Family Reference Model Generation

Malware family generation is the generation of comprehensive signatures used to identify one or more anomalous, or more specifically malicious, files, processes, etc., and/or relationships that are related through, among others, the evolution of a malware, a common point of attack or attack pattern (e.g., multiple pieces of malware gaining unauthorized access to the same file or process within an operating system), a common method of entering a network or electronic device (e.g., embedded software in an email or embedded software in a portable document format (PDF) file), a common targeted vulnerability (e.g., a common exploit kit), a common targeted information and/or a common targeted unauthorized access point. The generation of a malware family reference model may be triggered, for example, at predetermined time intervals, after receipt of a predetermined amount of data from the network 240, and/or manually by a system administrator or the like.

Upon the triggering of the generation of a malware family reference model, the gathering logic 212 of the machine learning logic 211 initially gathers a plurality of appropriate reference models stored in the machine learning data store 214. The gathering logic 212 determines which reference models are appropriate for generation of a malware family reference model based on one or more characteristics of the triggering event and/or the plurality of reference models currently stored in the machine learning data store 214. The matching logic 213 of the machine learning logic 211 compares the received data and the one or more reference models gathered by the gathering logic 212.

In one embodiment, the reference models stored in the machine learning data store 214 may all include one or more common events and/or relationships and therefore all reference models may be used to generate a family malware reference model. Alternatively, appropriate reference models for generating a malware family reference model may be selected based on file types included in the reference models and/or a source that observed the events included in the reference models (e.g., email TDS, web TDS, file TDS and/or mobile TDS). Furthermore, if a network administrator manually triggers the generation of a reference model, the network administrator may manually select one or more of the above characteristics for the gathering logic 212 to use in its determination of what reference models in the machine learning data store 214 are appropriate to include in the reference model generation.

Once the reference models that will be used to generate a malware family reference model have been gathered by the gathering logic 212, the reference models are passed to the reference model generating logic 215. As will be discussed below in relation to FIG. 9, the reference model generating logic 215 generates a malware family reference model by computing the mathematical union between the plurality of reference models gathered by the gathering logic 212.

Figure 9:
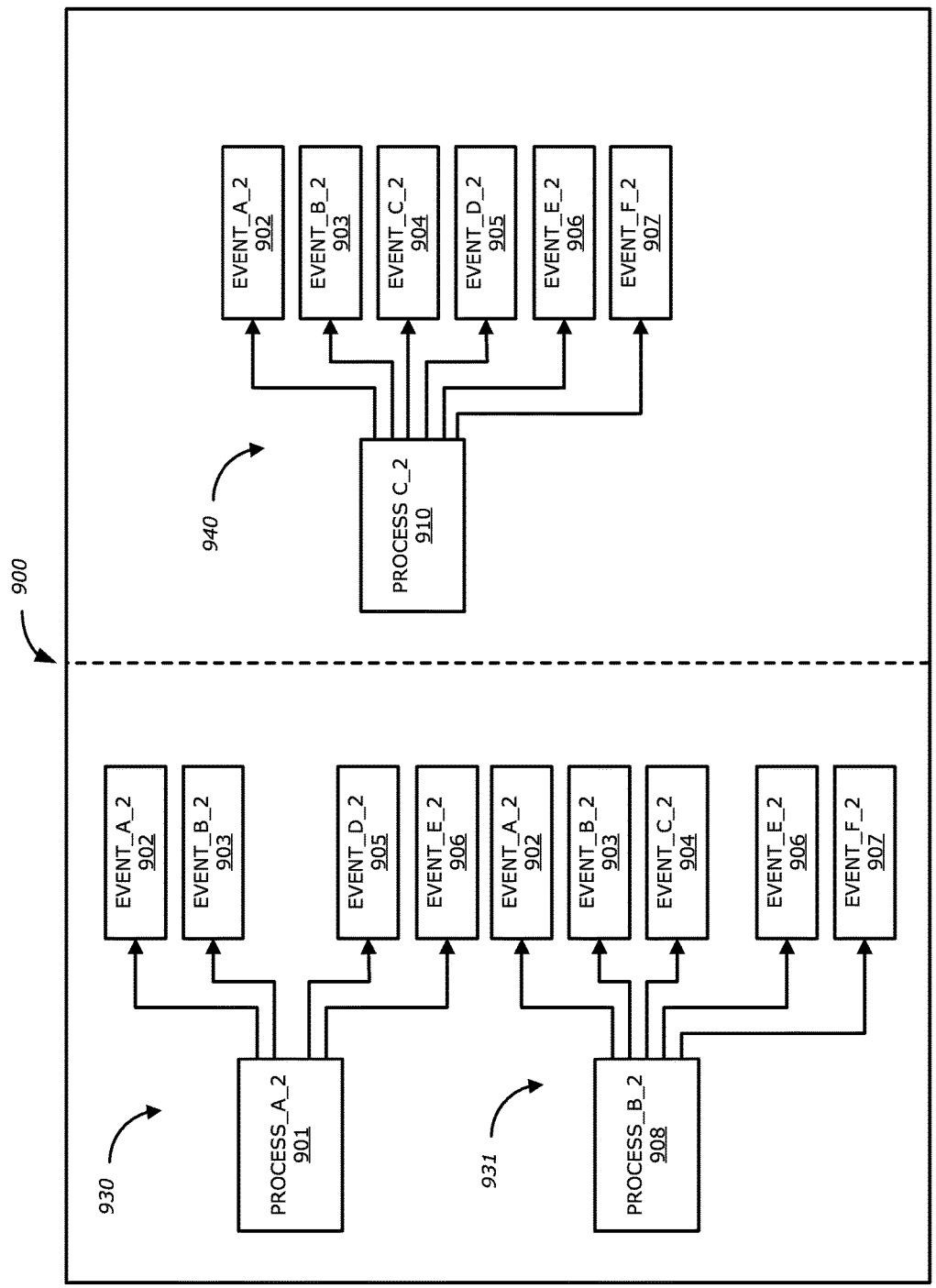
FIG. 9 is an exemplary illustration of a process of generating a malware family reference model.

Referring to FIG. 9, an exemplary illustration of a process of generating a malware family reference model is shown. The generation process 900 performed by the reference model generation logic 215 of FIG. 2 includes a left side and a right side. The left side includes two reference models, the reference models 930 and 931. The reference model 930 includes the Process_A_2 901 and the events Event_A_2 902, Event_B_2 903, Event_D_2 905 and Event_E_2 906. The reference model 931 includes the Process_B_2 908 and the events Event_A_2 902, Event_B_2 903, Event_C_2 904, Event_E_2 906 and Event_F_2 907.

The malware family reference model 940 has been generated from the reference models 930 and 931. The reference model generation logic 215 compares two or more reference models in order to generate a malware family reference model. The reference model generation logic 215 generates the malware family reference model by placing all distinct events in the two or more reference models compared (e.g., the mathematical union of the two or more reference models compared) into the malware family reference model (e.g., the malware family reference model 940).

As illustrated in FIG. 9, the malware family reference model 940 contains all distinct events included in the reference models 930 and 931. In particular, the reference model generation logic 215 generates the malware family reference model 940 by placing the events the reference model 930 has in common with the reference model 931 (the events Event_A_2 902, Event_B_2 903, Event_C_2 904 and Event_E_2 906) in the malware family reference model 940. The reference model generation logic 215 also places any events included in the reference model 930 in the malware family reference model 940 that are not included in the reference model 931 (the events Event_D_2 905). To conclude, the reference model generation logic 215 places any events included in the reference model 931 in the malware family reference model 940 that are not included in the reference model 930 (the events Event_F_2 907). The process of placing events in common or events included in less than all of the reference models compared to generate a malware family reference model may be done in any order.

The malware family reference model 940 also includes the process Process_C_2 910. This process may be equivalent to any of the processes included in one or more of the reference models compared to generate the malware family reference model (e.g., the processes Process_A_2 901 and Process_B_2 908).

The reference models used by the machine learning logic 211 to generate malware family reference models may be stored in the machine learning data store 214 and/or the event log 232, and/or received over the network 240. In addition, signatures generated in accordance with the discussion of FIGS. 14A and 14B may be used in the generation of malware family reference models.

C. Visualization

As mentioned above, interactive display screens comprising FIGS. 7A-7C may be generated by the display generation logic 211 of the UI rendering subsystem 220. In such an embodiment, the interactive display screens illustrating FIGS. 7A-7C may give a viewer a side-by-side visual comparison of a reference model and an association of potentially malicious events (e.g., at least a portion of data received over the network 240). A side-by-side visual comparison may allow a viewer to understand the source of the anomalous behavior as well as determine what files, processes, network settings, etc., and/or relationships that may have been affected.

Figure 10:
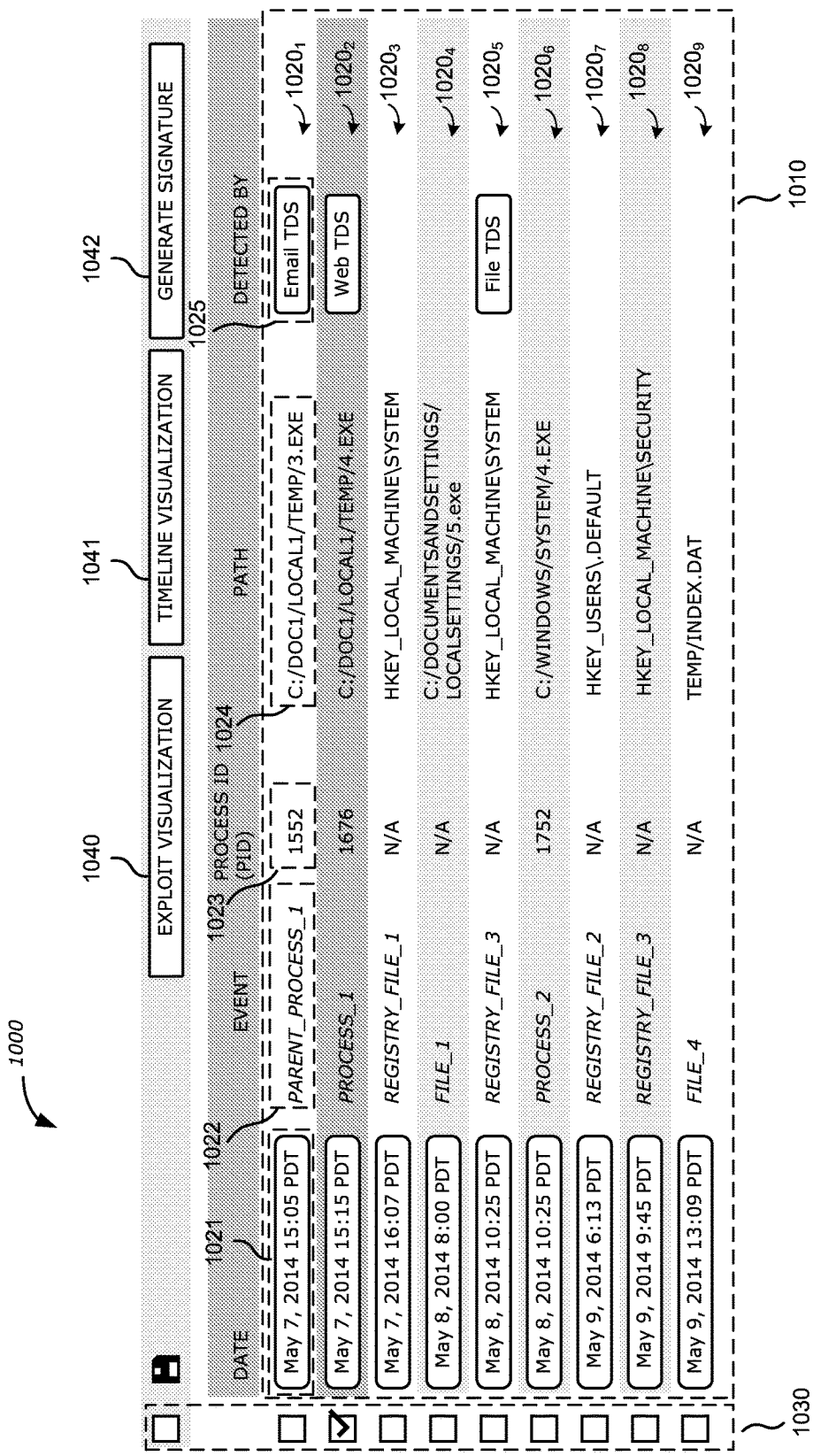
FIG. 10 is an exemplary embodiment of an interactive display screen for display of associated events and/or particulars of the associated events used in generating the interactive display screens of FIGS. 12-14B.

Referring to now FIG. 10, an exemplary embodiment of an interactive display screen 1000 for display of associated events and/or particulars of the associated events used in generating the interactive display screens of FIGS. 12-14B is shown. Herein, rendered by the UI rendering subsystem 220, the interactive display screen 1000 features a plurality of display areas 1010 and 1030 that illustrate information directed to events and particulars of the observed events over a time period by the one or more sources (the endpoint devices 250₁ and 250₂, the TDSes 260₁-260₃ and/or the cloud computing services 241 of FIG. 2) and or the management system 242 of FIG. 2.

According to one embodiment, the display area 1010 displays a plurality of entries 1020₁-1020ᴿ (R≥1, where R=9 for this embodiment) that provides information directed to observed events, where one or more events are anomalous or malicious. As shown, each row of entries (e.g., row 1020₁) rendered by the UI rendering subsystem 220 features a plurality of fields, including one or more of the following: (1) a date and time of the observation 421; (2) an event name 422; (3) a process identification (PID) 423 (if applicable); (4) a path directing the viewer to the location at which the event may be located 424; and/or (5) a source that observed the event (e.g., email TDS, web TDS, file TDS and/or mobile TDS).

A second area 1030 may be configured to allow selection of one or more observed potentially malicious events for viewing on a second visual representation. In one embodiment, when an observed event has been selected, the row may appear highlighted as is seen in FIG. 10. The buttons 1040 and 1041 enable viewing of an interactive visual representation (e.g., nodal diagram) of the selected events as they relate to one or more events within the display area 1010 and/or as they compare to one or more reference models of known anomalous or malicious behaviors. For example, based on the exemplary embodiment of FIG. 10 in which entry 1020₂ is selected, activation of the button 1040 labeled "Exploit Visualization" would subsequently present an interactive display screen of the relationships of the observed event represented in entry 1020₂ to other events, including perhaps one or more events appearing in display area 1010 (to be described below). Similarly, activation of the button 1041 labeled "Timeline Visualization" would subsequently present a second interactive display screen of the relationships of the observed event represented in the selected entry 1020₂ to other events, including perhaps one or more events appearing in display area 1010 (to be described below). Alternatively, activation of the button 1042 labeled "Generate Signature" would request the machine learning logic 211 of FIG. 2 to generate a signature based on the selected event and, in one embodiment, any subsequent events branching from the selected event (to be discussed in detail below).

Figure 12:
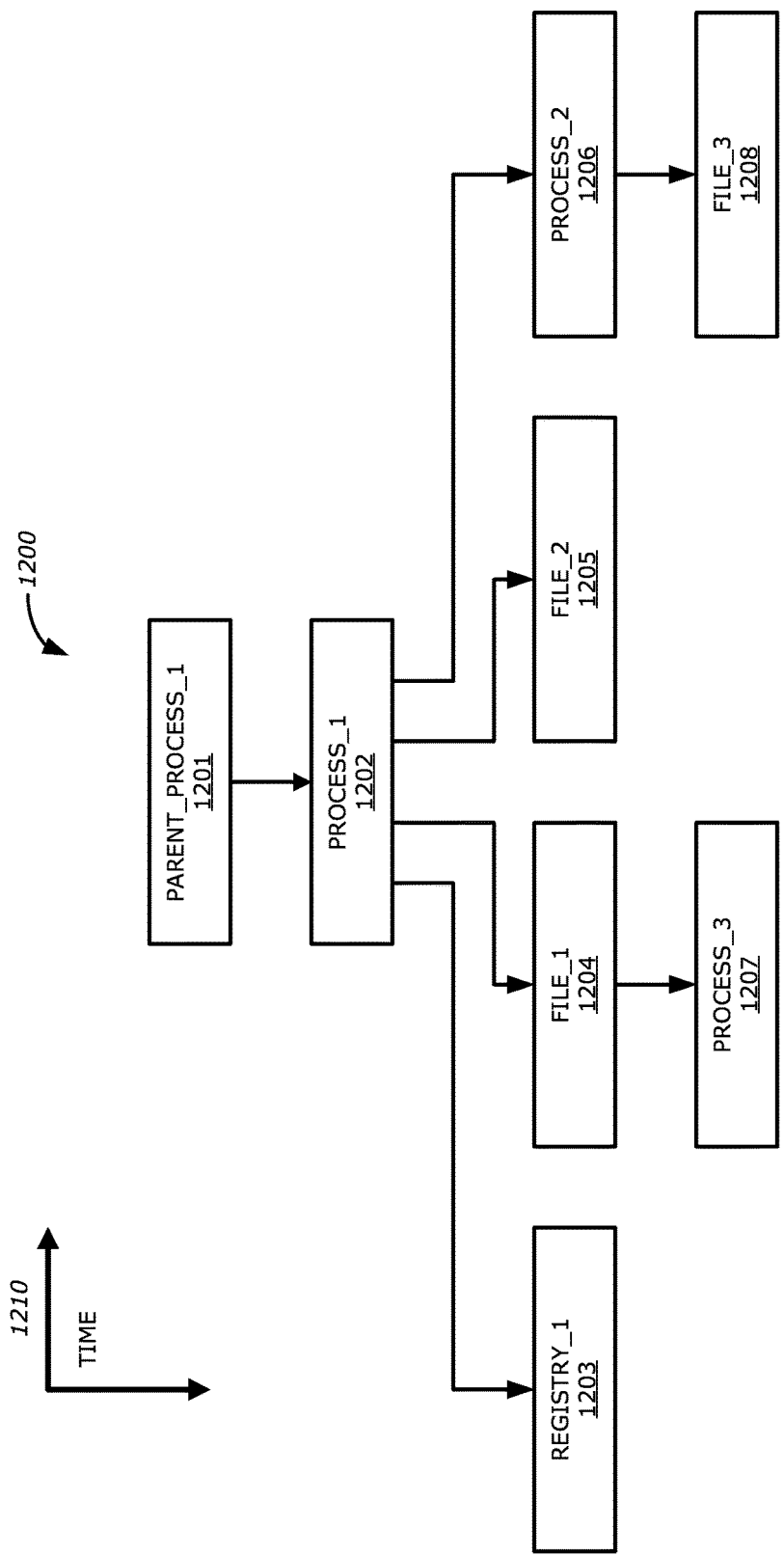
FIG. 12 is an exemplary illustration of a first embodiment of an interactive display screen for display of associated events and particulars of the associated events.

One or more interactive display screens may be comprised of, among other things, a top-down nodal or tree diagram (e.g., an "exploit visualization") or a left-to-right nodal or tree diagram (e.g., "a timeline visualization"). A time axis is illustrated in FIG. 12 and will be discussed below. Particulars of the events may be included to provide a detailed understanding of, among other things, where events are located within an electronic device or various methods of identifying one or more events (e.g., file/process name or PID). In addition, the interactive display screen may provide the viewer an understanding of how the event was detected by color-coding the events or providing various line formatting (e.g., dashed lines, solid lines, double lines, etc.) based on, for example, the portion of a TDS or endpoint device that observed the event. Alternatively, the illustration of the events may be color-coded based on the type of event. Additionally, the display may be a static visual representation of the one or more relationships between one or more events.

In addition, a rank may be assigned to the events included in a nodal diagram. For example, when an association of events are illustrated as a top-down nodal diagram, each row of events may be considered to have the same rank, wherein a first event appearing above a second event has a higher rank than the second event. Alternatively, when an association of events are illustrated as a left-to-right nodal diagram, each column of events may be considered to have the same rank, wherein a first event appearing to the left of a second event has a higher rank than the second event.

Referring to FIG. 11, an exemplary portion of data generated by either the reference model generating logic 215 or the machine learning logic 211 expressed in XML is shown. As described above, the machine learning logic 211 generates interactive display screen information for the visual representation of one or more relationships between one or more events and the particulars of the events. FIG. 11 illustrates one embodiment of data detailing the relationship of a first event to a second event and the relationship of the first event to a third event. For example, lines 5-6 denote the first and second events (node 1 and node 2 as "process_1" and "registry_1," respectively). Line 9 denotes the relationship before the first and second events (edge 1 as "node_1.created/changed-properties.node_2"). Similarly, Lines 12-20 represent details of the relationship between the first event and the third event.

The data illustrated as FIG. 11 may represent the interactive display screen information used by the display generation logic 221 to generate a display for viewer. For example, the data illustrated in FIG. 11 is used by the display generation logic 221 to generate a portion of FIGS. 12 and 13 as discussed below.

Referring now to FIG. 12, an exemplary illustration of a first embodiment of an interactive display screen for display of associated events and particulars of the associated events is shown. In FIG. 12, the interactive display screen 1200, depicted as a nodal diagram, illustrates the associated events at a high-level allowing a viewer to obtain an understanding of the relationships between one or more observed events wherein one or more anomalous behaviors are present. An anomalous behavior may be (i) a suspicious event or relationship that was observed by one or more of the sources (the endpoint devices 250₁ and 250₂, the TDSes 260₁-260₃ and/or the cloud computing services 241) or (ii) a malicious event or relationship observed by one or more of the sources. For example, a malicious event may cause performance of one or more actions that result in one or more malicious behaviors and/or one or more non-malicious behaviors. In general, the depiction of a first event appearing vertically above a second event is intended to illustrate that the first event was observed at a time prior to the second event. Similarly, a depiction of a second event appearing vertically equivalent (e.g., aligned in a row) with a third event, wherein the second event appears to the left of the third event, is intended to illustrate that the second event was observed at a time prior to the third event. It should be noted that exceptions may occur and labeling of such exceptions (e.g., by the use of numbering events and/or relationships) may be used to denote such exceptions to the viewer (numbering of exceptions will be illustrated in and described along with FIG. 13).

In FIG. 12, the Parent_Process_1 1201 is seen to cause an action or operation resulting in the Process_1 1202 at a first time. In one embodiment, the Parent_Process_1 1201 may be a malicious event and starting the Process_1 1202 may constitute a malicious action or operation (e.g., if the Process_1 1202 is also a malicious event and/or if the starting of the Process_1 1202 was not a normal function of the electronic device on which the action or operation occurred (or virtual machine performing processing of the Parent_Process_1 1201)). Alternatively, the Parent_Process_1 1201 and/or the Process_1 1202 may be non-malicious events and the starting of the Process_1 1202 may be construed as a non-malicious action or operation.

In addition, the Process_1 1202 causes the performance of one or more actions or operations that result in the events including: (i) the Registry_1 1203; (ii) the File_1 1204; (iii) the File_2 1205; and (iv) the Process_2 1206. Similarly, the File_1 1204 is depicted as causing the performance of an action or operation that results in the Process_3 1207. Furthermore, the Process_2 1206 is depicted as causing the performance of an action or operation that results in the File_3 1208.

Therefore, according to one embodiment, when the interactive display screen 1000 of FIG. 10 is viewed and the button 1440 ("Exploit Visualization") is activated, the interactive display screen 1200 is displayed using the information included in the interactive display screen 1000 which may be derived from interactive display screen information expressed as XML files similar to FIG. 11.

As mentioned above, a time axis 1210 is illustrated in FIG. 12. The time axis 1210 illustrates the embodiment wherein an interactive display screen (e.g., the interactive display screen 1200) is configured to illustrate an order of events in a sequential manner according to one or more time axes. The time axis 1210 shows that the events in the interactive display screen 1200 are ordered in a top-to-bottom and left-to-right manner according to the time of performance of the one or more actions or operations that resulted in the events 1201-1208. For example, the event 1202 is illustrated below the event 1201 implying that the performance of the one or more actions or operations that resulted in the event 1201 occurred prior in time to the one or more actions or operations that resulted in the event 1202. Similarly, the event 1203 is illustrated to the left of the event 1204 implying that the performance of the one or more actions or operations that resulted in the event 1203 occurred prior in time to the one or more actions or operations or behaviors that resulted in the event 1204. In another embodiment, a time axis may only comprise one axis (e.g., horizontal such as left-to-right, vertical such as top-to-bottom, etc.). Alternatively, a time axis may not be included in an interactive display screen.

In addition, a time axis may be present in an interactive display screen illustrating a left-to-right nodal diagram (e.g., an embodiment in which FIG. 7D may be used as an interactive display screen). As stated above, when a time axis is present in an interactive display screen illustrating a left-to-right nodal diagram, the time axis may comprise a single axis (e.g., only top-to-bottom) or may comprise two time axes (e.g., top-to-bottom and left-to-right).

Referring back to FIG. 2, the machine learning engine 210 analyzing observed events comprising an exploit after the occurrence of the exploit may fail to determine the source of infection. Even if the events are observed in their entirety, sometimes the voluminous manner of the observed events (events comprising both malicious events and non-malicious events) may make the determination of the presence of an exploit and/or malware difficult. Being able to compare the observed events with a reference model assists in sifting through the data and discovering the origin of infection. For example, a user may have browsed to a well-known Uniform-Resource Locator (URL) that was compromised and unintentionally downloaded malware on an endpoint. Subsequently, the malware may have stolen data and uploaded the stolen data to a foreign server. A reference model stored in the MDVS 200 may contain the sequence of such events.

If the matching logic 213 of the MDVS 200 is able to match the observed events with a portion of the reference model, the machine learning logic 211 may infer that all of the events occurred although not all of the events were observed based on the sequential ordering of the reference model. The matching logic 213 may determine that one or more events in the reference model were not observed, or were not observed with at least a first confidence. For example, based on the sequential ordering of the events and the time axis of the reference model, the machine learning logic 211 may infer that an event_B occurred prior to an event_C but subsequent to an event_A, although event_B was not observed by at least one source (e.g., the endpoint device $250_1$).

In addition, the machine learning logic 211 may trace the root cause of the exploitation back to the initial visit to the compromised URL based on a time axis and the sequential ordering of the events in the reference model. In one embodiment, the presence of a time axis on an interactive display screen may allow a viewer, such as a network administrator, to visually understand which event was the root cause of the exploit.

Figure 13:
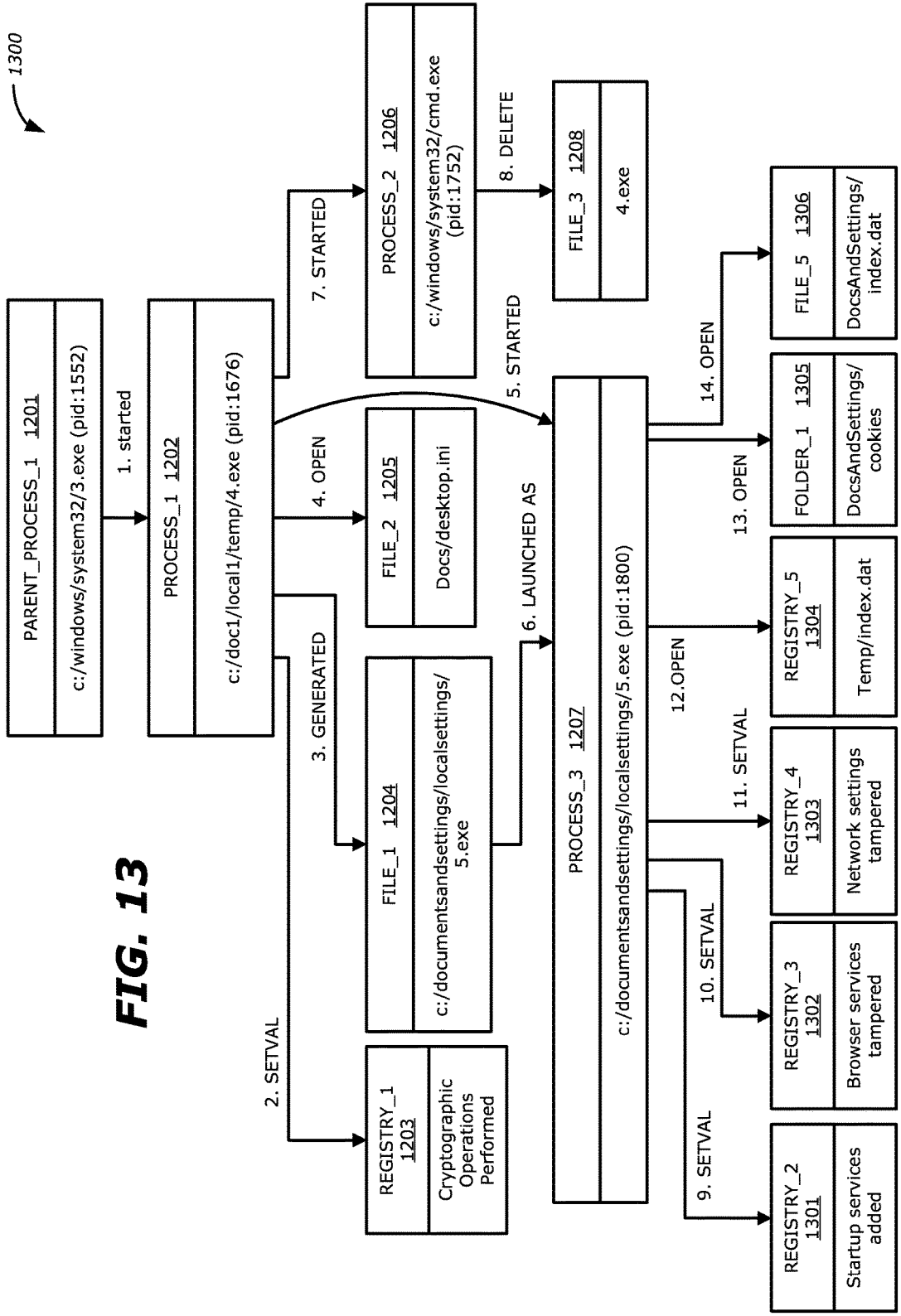
FIG. 13 is an exemplary illustration of a detailed embodiment of the interactive display screen of FIG. 12.

Referring to FIG. 13, an exemplary illustration of a detailed embodiment of the interactive display screen of FIG. 12 is shown. In addition to events 1201-1208 of FIG. 12, interactive display screen 1300 illustrates events 1301-1306 corresponding to the Registry_2, the Registry_3, the Registry_4, the File_4, the Folder_1 and the File_5, respectively. In particular, the Process_3 1207 causes the performance of one or more actions or operations that result in events 1301-1306.

In addition to providing a visual representation of how the events 1201-1208 and 1301-1306 are related, the interactive display screen 1300 displays one or more particulars of each event. For example, the path ("c:/doc1/local1/temp/4.exe") and the PID ("1676") are displayed for the Process_1 1202. The particulars displayed for each event may differ, for example, only the path of an event may be displayed as is the case with the File_1 1204 in the present embodiment.

Furthermore, the interactive display screen 1300 provides the viewer with the relationship between two events and the timing of the observation of the relationship. For example, the relationship between the Process_1 1202 and the File_1 1208 is the third relationship generated of the relationships displayed in the interactive display screen 1300. In addition, the relationship between the Process_1 1202 and the File_1 1208 is seen to be "created." Therefore, from the interactive display screen 1300, a viewer can easily determine that, of the events and relationships included in the display screen 1300, the operation of the Process_1 1202 creating the File_1 1204 was the third relationship created. The Process_1 1202 then opens the File_2 1205 and starts the Process_3 1207 (which is the File_1 1204 being launched as a process as the File_1 1204 is an executable file). In addition, the Process_1 1202 starts the Process_2 1206 as the seventh relationship.

The Process_2 1206 deletes the File_3 1208 as the eighth relationship. Subsequently, the Process_3 1207 sets the name/value pair for the Registry_2, the Registry_3 and the Registry_4 as the ninth, tenth and eleventh relationships respectively. The Process_3 1207 then opens the Registry_5, the Folder_1 and the File_5 as the twelfth, thirteenth and fourteenth relationships respectively.

V. Signature Generation

As mentioned above, one embodiment of the invention enables a viewer to generate one or more signatures from the interactive display screens of, for example, FIGS. 10 and 12-14B. In one embodiment, the viewer may select an event and generate a signature based on the event including any events that directly and/or indirectly branched from the selected event. In a second embodiment, the viewer may select a particular grouping of events and generate a signature limited to those selected events. The generated signatures may be stored in the machine learning data store 214 of FIG. 2 to be used in future comparisons of one or more reference models of a plurality of events and at least one or more relationships where at least one of these events and/or relationships is an anomalous behavior or known to be malicious. In addition, signatures generated from a first set of data received from a first endpoint device may be compared to similar signatures generated from a second set of data received from a second endpoint device in order to determine whether an event frequently appears across multiple endpoint devices (e.g., correlated operations or actions across endpoint devices). The frequent appearance of an event across multiple endpoint devices may imply that the event is malicious (e.g., an exploit), or at least suspicious. In addition, the frequent appearance of one or more events across multiple endpoint devices (or other sources that supply data to the MDVS 200) may indicate that the one or more sources is associated with a malware family.

Figure 14A:
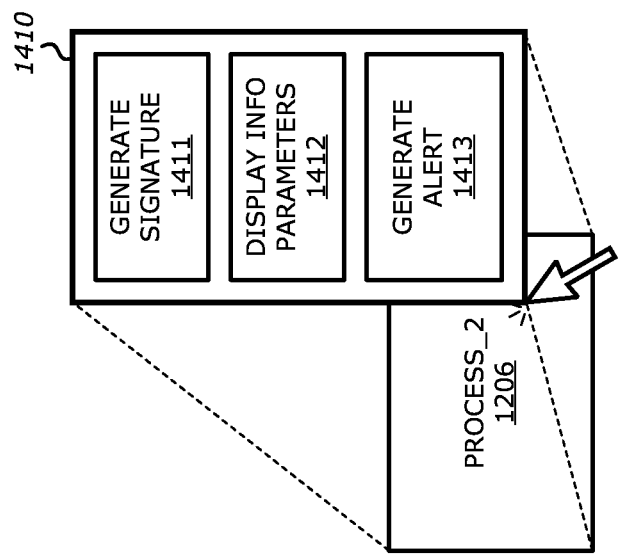
FIG. 14A is an exemplary illustration of a portion of an interactive display screen for enabling a viewer to generate a signature of a selected event, display particulars of the selected event and/or generate an alert for a selected event.

Referring to FIG. 14A, an exemplary illustration of a portion of an interactive display screen for enabling a viewer to generate a signature of a selected event, display particulars of the selected event and/or generate an alert for a selected event is shown. FIG. 14A illustrates a viewer selecting an event (e.g., the Process_2 1206 of FIG. 12) which brings up an overlaying pop-up box 1410 allowing the viewer to select to "Generate Signature 1411," "Display Info Parameters 1412" or "Generate Alert 1413." The selection of "Generate Signature 1411" enables the viewer to generate a signature (e.g., a reference model) based on the selected event. The signature may include all events that are a direct or indirect branch from the selected event. For example, a viewer selecting "Generate Signature 1411" for the Process_2 1206 may generate a signature including the Process_2 1206 and the File_3 1208 (as is seen in FIG. 12). The selection of "Display Info Parameters 1412" for the Process_2 1206 would display an interactive display screen including the information included in the row 1020₆ of FIG. 10. The selection of "Generate Alert 1413" enables a viewer to generate a rule for the MDVS 200 to issue an alert when the selected event is observed by an endpoint device or other source. Therefore, according to the example in FIG. 14A, when a viewer selects "Generate Alert 1413" for the Process_2 1206, the MDVS 200 will issue an alert to the viewer notifying the viewer of the observation of the Process_2 1206 at an endpoint device. In one embodiment, the MDVS 200 will issue the alert when the MDVS 200 receives data containing an observation of the Process_2 1206. In a second embodiment, the MDVS 200 may notify the management system 242 of the creation of the rule and the management system 242 may propagate the rule to each source connected to the network 240 (the endpoint devices 250₁-250₂, the TDS 260₁-260₃ and the cloud computing services 241).

Referring back to FIG. 1, the selection of one or more of "Generate Signature 1411," "Display Info Parameters 1412" or "Generate Alert 1413" is equivalent to the "Interactive Display Screen Input" illustrated in FIG. 1. The interactive display screen input is transmitted from block 150 to block 120. In particular, the data obtained from the selecting "Generate Signature 1411" includes the particulars of the selected event (e.g., the Process_2 1206 as seen in FIG. 14A) and potentially the events branching from the selected event and the relationships that connect the selected event and any branched events. This data obtained from the selection of "Generate Signature 1411" may be stored as a signature/reference model in the machine learning data store 214 for use in future exploit detection processes and/or reference model generation processes.

The selection of "Display Info Parameters 1412" may result in a query by the gathering logic 212 to the machine learning data store 214 and/or the event log 232 to gather the particulars of the selected process. The machine learning logic 211 may generate interactive display screen information based on the data gathered by the gathering logic 212. The display generation logic 221 may use the interactive display screen information to generate a display in a layout similar to the display screen of FIG. 10.

The selection of "Generate Alert 1413" may result in the gathering of the particulars of the selected process, any events that are branched from the selected event and any relationships connecting the branched events by the gathering logic 212 and the generation of an alert by the machine learning logic 211.

It should be noted that, although in the above paragraphs information (e.g., the particulars) of branched events and the corresponding relationships may be gathered as well as the selected event, the particulars of only the selected event may be gathered as well. The system may be set up to gather either, or a network administrator may be able to adjust how the system responds to a selection of one or more of "Generate Signature 1411," "Display Info Parameters 1412" and/or "Generate Alert 1413."

Figure 14B:
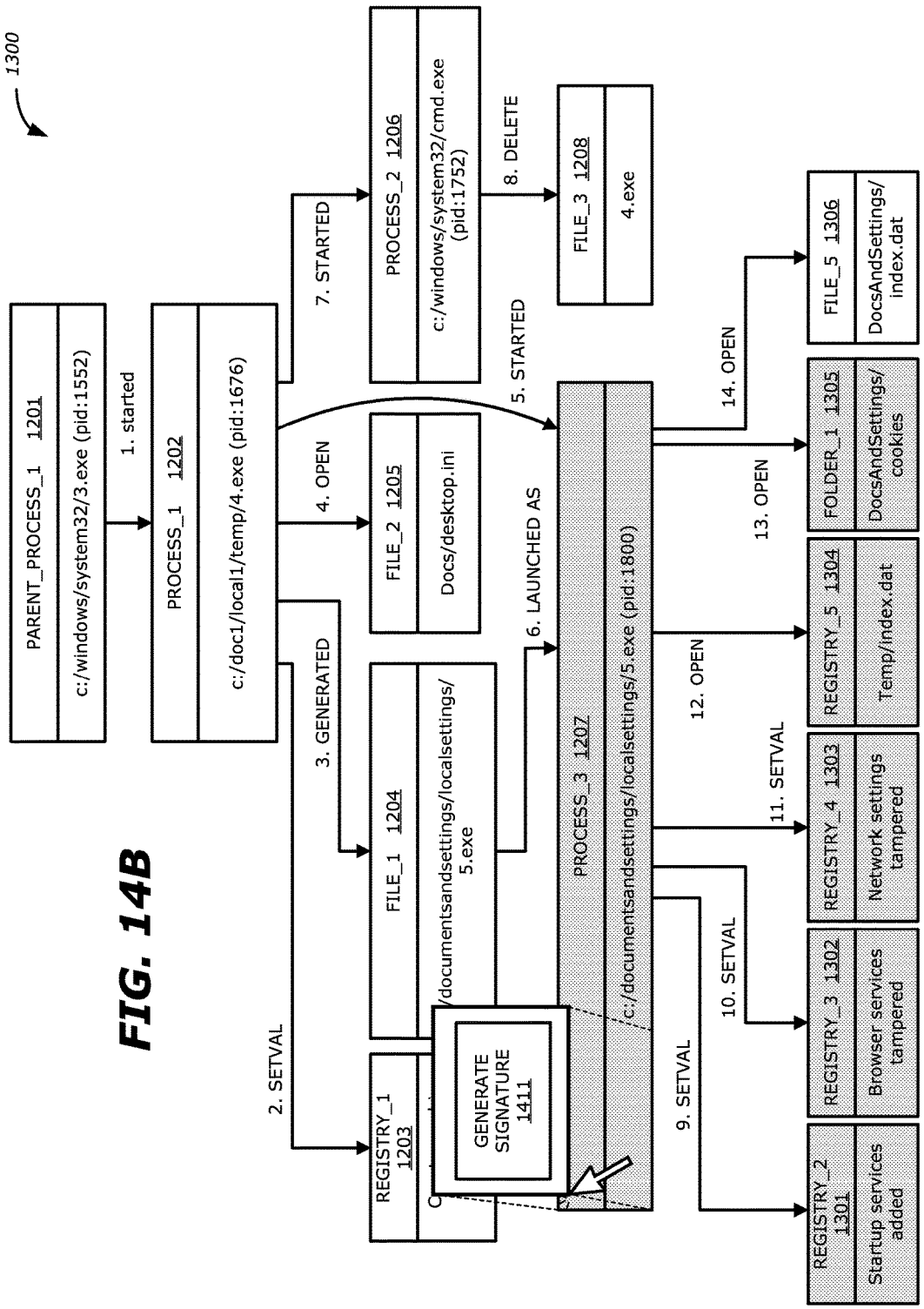
FIG. 14B is an exemplary illustration of a second embodiment of an interactive display screen for enabling a viewer to generate a signature of a selected event.

Referring to FIG. 14B, an exemplary illustration of a second embodiment of an interactive display screen for enabling a viewer to generate a signature of a selected event is shown. FIG. 14B illustrates that a viewer has selected a particular grouping of events (the Process_3, the Registry_2, the Registry_3, the File_4 and the Folder_1) for which the viewer may generate a signature by selecting "Generate Signature 1411." The generated signature in FIG. 14B differs slightly from that of FIG. 14A in the sense that the signature of 14A may include all of the events branching directly and/or indirectly from the selected from. FIG. 14B does not include the event File_5 1406. The exclusion of the event File_5 1406 may be a result of the viewer knowing whether the event File_5 1406 are not malicious and therefore should be not included in a reference model. The selection of "Generate Signature 1411" in FIG. 14B has the same effect as discussed in reference to FIG. 14A above.

Referring to FIG. 15, is an exemplary portion of the generated signature (corresponding to the selected section in FIG. 14B) expressed in XML. The data illustrated by FIG. 15 represents the XML generated when a viewer generates a signature from the interactive display screen 1300 as illustrated in FIG. 14B. As seen in FIG. 14B, a portion of the interactive display screen 1300 has been manually selected by a user and an input (e.g., clicking of a button on a mouse) allows the viewer to generate a signature by activating the option labeled "Generate Signature" 1411. The data illustrated in FIG. 15 may be stored in the machine learning data store 214 and used by the reference model generation logic 215 and/or the matching logic 213 to either generate a reference model or perform an exploit detection process, respectively.

In the foregoing description, the invention is described with reference to specific exemplary embodiments thereof. It will, however, be evident that various modifications and changes may be made thereto without departing from the broader spirit and scope of the invention as set forth in the appended claims.

What is claimed is:

1. A system for cyber-attack detection comprising:
one or more hardware processors; and
a non-transitory storage module communicatively coupled to the one or more processors, the storage module comprises logic, upon execution by the one or more processors, that
  accesses a first set of information that comprises (i) information directed to a plurality of observed events, each of the observed events being observed during operation of a source device communicatively coupled to the system, and (ii) information directed to one or more relationships that identify an association between different observed events, wherein each of the one or more relationships comprises a connection that occurs during computer processing between at least two events and wherein each of the plurality of observed events is an action or operation resulting from an execution of code,
  generates a reference model based on the first set of information, the reference model comprises at least a first observed event, a second observed event, and a first relationship that identifies that the second observed event is based on the first observed event, wherein the first observed event and the second observed event are included in the plurality of observed events,
  analyzes a second set of information that is different than the first set of information, the second set of information including a third event and a second relationship,
  enhances the reference model by adding the third event or the second relationship to the reference model based on a correlation between the reference model and the second set of information, and
  generates an interactive graphical display of at least the reference model that includes the third event or the second relationship,
  wherein a combination of events and relationships comprising the reference model indicate a cyber-attack.

2. The system of claim 1, wherein the anomalous behavior includes a first file opened by a first process, wherein the first file is configured to be opened by a second process that is different from the first process and is not configured to be opened by the first process.

3. The system of claim 1, wherein the generating of the reference model by the logic comprises determining that the first event of the plurality of observed events performed at least one of an action or an operation, the at least one of the action or the operation results in an observance of subsequent events of the plurality of observed events including the second event of the plurality of observed events.

4. The system of claim 1, wherein the source device is one of an endpoint device, a threat detection system, or a cloud computing service.

5. A system for cyber-attack detection comprising:
one or more hardware processors; and
a non-transitory storage module communicatively coupled to the one or more processors, the storage module comprises (i) an event log to store information associated with at least a first plurality of observed events and (ii) logic that, upon execution by the one or more processors and in response to a triggering event,
  (a) accesses a first set of information that comprises (i) information directed to the first plurality of observed events stored in the storage, each of the first plurality of observed events being observed during operation of a source device communicatively coupled to the system, and (ii) information directed to one or more relationships that identify an association between different observed events, wherein each of the one or more relationships comprises a connection that occurs during computer processing between at least two events and wherein each of the plurality of observed events is an action or operation resulting from an execution of code,
  (b) accesses a reference model based on a second plurality of observed events, the reference model comprises at least a first observed event of the second plurality of observed events, a second observed event of the second plurality of observed events, and a first relationship that identifies that the second event is based on the first event, wherein the first observed event and the second observed event are included in the plurality of observed events,
  (c) enhances the reference model by adding a third event or a second relationship to the reference model based on a correlation between the reference model and the first set of information, the third event and the second relationship included in the first set of information, and
  (d) generates a graphical, interactive display of a comparison of the first plurality of observed events with the reference model that includes the third event of the second relationship, the interactive display including one or more diagrams,
  wherein a combination of events and relationships comprising the reference model indicate a cyber-attack.

6. The system of claim 5, wherein a first event of the first plurality of observed events is selectable to (i) provide metadata associated with the first event of the first plurality of observed events; (ii) generate a signature of the first event of the first plurality of observed events; or (iii) generate an alert for the first event of the first plurality of observed events.

7. The system of claim 6, wherein
at least the first event and a second event of the first plurality of observed events are selectable via the graphical interactive display.

8. The system of claim 5, wherein the plurality of diagrams include two or more nodal diagrams placed in a side-by-side manner, the nodal diagrams illustrating (i) each event of the first plurality of observed events and each relationship of the first plurality of observed events and (ii) the reference model.

9. The system of claim 5, wherein the first event of the first plurality of observed events is illustrated in the one or more diagrams with a solid line, the solid line representing that the first event of the first plurality of observed events was observed with at least a first confidence.

10. The system of claim 9, wherein the first event of the first plurality of observed events is illustrated in the one or more diagrams with a dotted line, the dotted line representing that the first event of the first plurality of observed events was observed with at least a second confidence but less than a first confidence, the first confidence being greater than the second confidence.

11. The system of claim 5, wherein the first relationship is illustrated in the one or more diagrams with a solid line, the solid line representing that the first relationship was observed with at least a first confidence.

12. The system of claim 5, wherein the first relationship is illustrated in the one or more diagrams with a dotted line, the dotted line representing that the first relationship was observed with at least a second confidence but less than a first confidence, the first confidence being greater than the second confidence.

13. The computerized system of claim 5, wherein the source device is one of an endpoint device, a threat detection system, or a cloud computing service.

14. A computerized method for malware detection comprising:
   accessing information that comprises (i) information directed to a plurality of observed events, each of the plurality of observed events being observed during operation of a source device communicatively coupled to the system, and (ii) information directed to one or more relationships identifying that a first observed event is based on a second observed event, wherein each of the one or more relationships comprises a connection that occurs during computer processing between at least two events and wherein each of the plurality of observed events is an action or operation resulting from an execution of code;
   generating an interactive display of at least the first observed event, the second observed event and a relationship identifying that the first observed event is based on the second observed event; and
   upon receiving a selection of the first observed event and the second observed event via the interactive display, generating a signature associating the first observed event and the second observed event, wherein combination of at least two of (i) the first observed event, (ii) the second observed event, or (iii) the relationship indicates known a cyber-attack.

15. The method of claim 13, wherein the signature associated with the first observed event and the second observed event further includes information associated with the relationship to identify that the first observed event is based on the second observed event.

16. The method of claim 13, wherein the interactive display comprises a nodal diagram illustrating at least the first observed event, the second observed event, and the relationship in a top-down, chronological sequence.

17. The method of claim 13, wherein the interactive display of the relationships comprises a nodal diagram illustrating at least the first observed event, the second observed event, and the relationship in a left-to-right, chronological sequence.

18. The computerized method of claim 14, wherein the source device is one of an endpoint device, a threat detection system, or a cloud computing service.

19. A system for cyber-attack detection comprising:
   one or more hardware processors; and
   a non-transitory storage module communicatively coupled to the one or more processors, the storage module comprises
   (i) an event log to receive and store a first set of information associated with a plurality of observed events and one or more relationships that identify an association between different observed events, each of the observed events being observed during operation of a source device communicatively coupled to the system, wherein each of the one or more relationships comprises a connection that occurs during computer processing between at least two events and wherein each of the plurality of observed events is an action or operation resulting from an execution of code,
   (ii) a machine learning data store to store one or more reference models,
   (iii) a machine learning logic that, upon execution by the one or more processors,
      (a) accesses the first set of information associated with the plurality of observed events, and
      (b) enhances a first reference model of the one or more reference models by adding a first event or a first relationship to the first reference model based on a correlation between the first reference model and the first set of information, the first event and the first relationship included in the first set of information, wherein a combination of events and relationships comprising the first reference model indicates a cyber-attack,
      (c) generates display screen information including a comparison of the first set of information and the first reference model that includes the first event or the first relationship; and
   (iv) a display generation logic that, upon execution by the one or more processors,
      (a) communicates with the machine learning logic, and
      (b) generates an interactive display screen from the display screen information including at least the first event or the first relationship.

20. The system of claim 17, wherein the first set of information includes at least two of (i) observations uncovered after virtual processing of a portion of network traffic under analysis by a virtual execution environment, (ii) observations uncovered after static processing of the portion of network traffic by a static analysis engine, and (iii) observations uncovered from monitored network traffic.

21. The system of claim 17, wherein enhancing the first reference model is performed when the third event and the second relationship were not previously present in the first reference model.

22. The system of claim 17, wherein the source device is one of an endpoint device, a threat detection system, or a cloud computing service.

23. A computerized method for malware detection comprising:
   accessing a first set of information that comprises (i) information directed to a plurality of observed events, each of the observed events being observed during operation of a source device communicatively coupled to the system, and (ii) information directed to one or more relationships that identify an association between different observed events, wherein each of the one or more relationships comprises a connection that occurs during computer processing between at least two events and wherein each of the plurality of observed events is an action or operation resulting from an execution of code,
   generating a reference model based on the first set of information, the reference model comprises at least a first observed event, a second observed event, and a first relationship that identifies that the second observed event is based on the first observed event, wherein the first observed event and the second observed event are included in the plurality of observed events, analyzing a second set of information that is different than the first set of information, the second set of information including a third event and a second relationship, enhancing the reference model by adding the third event or the second relationship to the reference model based on a correlation between the reference model and the second set of information, and generating an interactive graphical display of at least the reference model that includes the third event or the second relationship, wherein a combination of events and relationships comprising the reference model indicate a cyber-attack.

24. The method of claim 23, wherein the anomalous behavior includes a first file opened by a first process, wherein the first file is configured to be opened by a second process that is different from the first process and is not configured to be opened by the first process.

25. The method of claim 23, wherein the generating of the reference model by the logic comprises determining that the first event of the plurality of observed events performed at least one of an action or an operation, the at least one of the action or the operation results in an observance of subsequent events of the plurality of observed events including the second event of the plurality of observed events.

26. A non-transitory computer readable medium, when processed by a hardware processor, determines whether a first set of information indicates a presence of a cyber-attack, the non-transitory computer readable medium comprising:

a machine learning logic to:
(a) access a first set of information that comprises (i) information directed to a plurality of observed events, each of the observed events being observed during operation of a source device communicatively coupled to the system, and (ii) information directed to one or more relationships that identify an association between different observed events, wherein each of the one or more relationships comprises a connection that occurs during computer processing between at least two events and wherein each of the plurality of observed events is an action or operation resulting from an execution of code,
(b) generate a reference model based on the first set of information, the reference model comprises at least a first observed event, a second observed event, and a first relationship that identifies that the second observed event is based on the first observed event, wherein the first observed event and the second observed event are included in the plurality of observed events,
(c) analyze a second set of information that is different than the first set of information, the second set of information including a third event and a second relationship, and
(d) enhance the reference model by adding the third event or the second relationship to the reference model based on a correlation between the reference model and the second set of information; and a display generation logic to generate an interactive graphical display of at least the reference model that includes the third event or the second relationship, wherein a combination of events and relationships comprising the reference model indicate a cyber-attack.

27. The non-transitory computer readable medium of claim 26, wherein the anomalous behavior includes a first file opened by a first process, wherein the first file is configured to be opened by a second process that is different from the first process and is not configured to be opened by the first process.

28. The non-transitory computer readable medium of claim 26, wherein the generating of the reference model by the logic comprises determining that the first event of the plurality of observed events performed at least one of an action or an operation, the at least one of the action or the operation results in an observance of subsequent events of the plurality of observed events including the second event of the plurality of observed events.

29. A computerized method for malware detection comprising:

accessing a first set of information that comprises (i) information directed to a first plurality of observed events stored in a storage module, each of a first plurality of observed events being observed during operation of a source device, the storage module including an event log to store the information associated with at least the first plurality of observed events, and (ii) information directed to one or more relationships that identify an association between different observed events, wherein each of the one or more relationships comprises a connection, that occurs during computer processing, between at least two events and wherein each of the plurality of observed events is an action or operation resulting from an execution of code;

accessing a reference model based on a second plurality of observed events, the reference model comprises at least a first observed event of the second plurality of observed events, a second observed event of the second plurality of observed events, and a first relationship that identifies that the second event is based on the first event, wherein the first observed event and the second observed event are included in the plurality of observed events;

enhancing the reference model by adding a third event or a second relationship to the reference model based on a correlation between the reference model and the first set of information, the third event and the second relationship included in the first set of information; and generating a graphical, interactive display of a comparison of the first plurality of observed events with the reference model that includes the third event of the second relationship, the interactive display including one or more diagrams, wherein a combination of events and relationships comprising the reference model indicate a cyber-attack.

30. The method of claim 29, wherein a first event of the first plurality of observed events is selectable to (i) provide metadata associated with the first event of the first plurality of observed events; (ii) generate a signature of the first event of the first plurality of observed events; or (iii) generate an alert for the first event of the first plurality of observed events.

31. The method of claim 30, wherein at least the first event and a second event of the first plurality of observed events are selectable via the graphical interactive display.

32. The method of claim 29, wherein the plurality of diagrams include two or more nodal diagrams placed in a side-by-side manner, the nodal diagrams illustrating (i) each event of the first plurality of observed events and each relationship of the first plurality of observed events and (ii) the reference model.

33. The method of claim 29, wherein the first event of the first plurality of observed events is illustrated in the one or more diagrams with a solid line, the solid line representing that the first event of the first plurality of observed events was observed with at least a first confidence.

34. The method of claim 33, wherein the first event of the first plurality of observed events is illustrated in the one or more diagrams with a dotted line, the dotted line representing that the first event of the first plurality of observed events was observed with at least a second confidence but less than a first confidence, the first confidence being greater than the second confidence.

35. The method of claim 29, wherein the first relationship is illustrated in the one or more diagrams with a solid line, the solid line representing that the first relationship was observed with at least a first confidence.

36. The method of claim 29, wherein the first relationship is illustrated in the one or more diagrams with a dotted line, the dotted line representing that the first relationship was observed with at least a second confidence but less than a first confidence, the first confidence being greater than the second confidence.

37. A non-transitory computer readable medium, when processed by a hardware processor, determines whether a first set of information indicates a presence of a cyber-attack, the non-transitory computer readable medium comprising:
an event log to store information associated with at least a first plurality of observed events;
logic that:
(a) accesses a first set of information that comprises (i) information directed to the first plurality of observed events stored in the event log, each of the first plurality of observed events being observed during operation of a source device, and (ii) information directed to one or more relationships that identify an association between different observed events, wherein each of the one or more relationships comprises a connection, that occurs during computer processing, between at least two events and wherein each of the plurality of observed events is an action or operation resulting from an execution of code,
(b) accesses a reference model based on a second plurality of observed events, the reference model comprises at least a first observed event of the second plurality of observed events, a second observed event of the second plurality of observed events, and a first relationship that identifies that the second event is based on the first event, wherein the first observed event and the second observed event are included in the plurality of observed events, and
(c) enhances the reference model by adding a third event or a second relationship to the reference model based on a correlation between the reference model and the first set of information, the third event and the second relationship included in the first set of information; and
a display generation logic to generate a graphical, interactive display of a comparison of the first plurality of observed events with the reference model that includes the third event of the second relationship, the interactive display including one or more diagrams, wherein a combination of events and relationships comprising the reference model indicate a cyber-attack.

38. The non-transitory computer readable medium of claim 37, wherein a first event of the first plurality of observed events is selectable to (i) provide metadata associated with the first event of the first plurality of observed events; (ii) generate a signature of the first event of the first plurality of observed events; or (iii) generate an alert for the first event of the first plurality of observed events.

39. The non-transitory computer readable medium of claim 37, wherein at least the first event and a second event of the first plurality of observed events are selectable via the graphical interactive display.

40. The non-transitory computer readable medium of claim 37, wherein the plurality of diagrams include two or more nodal diagrams placed in a side-by-side manner, the nodal diagrams illustrating (i) each event of the first plurality of observed events and each relationship of the first plurality of observed events and (ii) the reference model.

41. The non-transitory computer readable medium of claim 37, wherein the first event of the first plurality of observed events is illustrated in the one or more diagrams with a solid line, the solid line representing that the first event of the first plurality of observed events was observed with at least a first confidence.

42. The non-transitory computer readable medium of claim 41, wherein the first event of the first plurality of observed events is illustrated in the one or more diagrams with a dotted line, the dotted line representing that the first event of the first plurality of observed events was observed with at least a second confidence but less than a first confidence, the first confidence being greater than the second confidence.

43. The non-transitory computer readable medium of claim 37, wherein the first relationship is illustrated in the one or more diagrams with a solid line, the solid line representing that the first relationship was observed with at least a first confidence.

44. The non-transitory computer readable medium of claim 37, wherein the first relationship is illustrated in the one or more diagrams with a dotted line, the dotted line representing that the first relationship was observed with at least a second confidence but less than a first confidence, the first confidence being greater than the second confidence.

45. A computerized method for malware detection comprising:
receiving and storing, by an event log, a first set of information associated with a plurality of observed events and one or more relationships that identify an association between different observed events, each of the observed events being observed during operation of a source device, wherein each of the one or more relationships comprises a connection that occurs during computer processing between at least two events and wherein each of the plurality of observed events is an action or operation resulting from an execution of code;
accessing, by a machine learning logic, the first set of information associated with the plurality of observed events;
enhancing, by a machine learning logic, a first reference model of one or more stored reference models by adding a first event or a first relationship to the first reference model based on a correlation between the first reference model and the first set of information, the first event and the first relationship included in the first set of information, wherein the one or more reference models including the first reference model are stored in a machine learning data store, wherein a combination of events and relationships comprising the first reference model indicates a cyber-attack;
generating, by a machine learning logic, display screen information including a comparison of the first set of information and the first reference model that includes the first event or the first relationship;
communicating, by a display generation logic, with the machine learning logic; and generating, by the display generation logic, an interactive display screen from the display screen information including at least the first event or the first relationship.

46. The computerized method of claim 45, wherein the first set of information includes at least two of (i) observations uncovered after virtual processing of a portion of network traffic under analysis by a virtual execution environment, (ii) observations uncovered after static processing of the portion of network traffic by a static analysis engine, and (iii) observations uncovered from monitored network traffic.

47. The computerized method of claim 45, wherein enhancing the first reference model is performed when the third event and the second relationship were not previously present in the first reference model.

48. The computerized method of claim 45, wherein the source device is one of an endpoint device, a threat detection system, or a cloud computing service.

49. A non-transitory computer readable medium, when processed by a hardware processor, determines whether a first set of information indicates a presence of a cyber-attack, the non-transitory computer readable medium comprising:
  an event log to receive and store a first set of information associated with a plurality of observed events and one or more relationships that identify an association between different observed events, each of the observed events being observed during operation of a source device, wherein each of the one or more relationships comprises a connection that occurs during computer processing between at least two events and wherein each of the plurality of observed events is an action or operation resulting from an execution of code;
  a machine learning data store to store one or more reference models;
  a machine learning logic to (a) access the information associated with the plurality of observed events, and (b) enhance a first reference model of the one or more reference models by adding a first event or a first relationship to the first reference model based on a correlation between the first reference model and the first set of information, the first event and the first relationship included in the first set of information, wherein a combination of events and relationships comprising the first reference model indicates a cyber-attack, (c) generate display screen information including a comparison of the first set of information and the first reference model that includes the third event or the second relationship; and
  a display generation logic to (a) communicate with the machine learning logic, and (b) generate an interactive display screen from the display screen information, including the first event or the first relationship .

50. The non-transitory computer readable medium of claim 49, wherein the first set of information includes at least two of (i) observations uncovered after virtual processing of a portion of network traffic under analysis by a virtual execution environment, (ii) observations uncovered after static processing of the portion of network traffic by a static analysis engine, and (iii) observations uncovered from monitored network traffic.

51. The non-transitory computer readable medium of claim 50, wherein enhancing the first reference model is performed when the third event and the second relationship were not previously present in the first reference model.

52. The non-transitory computer readable medium of claim 51, wherein the source device is one of an endpoint device, a threat detection system, or a cloud computing service.

* * * * *

UNITED STATES PATENT AND TRADEMARK OFFICE
CERTIFICATE OF CORRECTION

PATENT NO. : 10,027,689 B1
APPLICATION NO. : 14/500587
DATED : July 17, 2018
INVENTOR(S) : Hirendra Rathor et al.

Page 1 of 1

It is certified that error appears in the above-identified patent and that said Letters Patent is hereby corrected as shown below:

In the Claims

Column 27, Lines 42-58, should read:

15. The method of claim 14, wherein the signature associated with the first observed event and the second observed event further includes information associated with the relationship to identify that the first observed event is based on the second observed event.

16. The method of claim 14, wherein the interactive display comprises a nodal diagram illustrating at least the first observed event, the second observed event, and the relationship in a top-down, chronological sequence.

17. The method of claim 14, wherein the interactive display of the relationships comprises a nodal diagram illustrating at least the first observed event, the second observed event, and the relationship in a left-to-right, chronological sequence.

Column 28, Lines 33-46, should read:

20. The system of claim 19, wherein the first set of information includes at least two of (i) observations uncovered after virtual processing of a portion of network traffic under analysis by a virtual execution environment, (ii) observations uncovered after static processing of the portion of network traffic by a static analysis engine, and (iii) observations uncovered from monitored network traffic.

21. The system of claim 19, wherein enhancing the first reference model is performed when the third event and the second relationship were not previously present in the first reference model.

22. The system of claim 19, wherein the source device is one of an endpoint device, a threat detection system, or a cloud computing service.

Signed and Sealed this
Seventeenth Day of March, 2020

Andrei Iancu
*Director of the United States Patent and Trademark Office*